United States Patent [19]

Van Rie et al.

[11] Patent Number: 5,659,123

[45] Date of Patent: Aug. 19, 1997

[54] DIABROTICA TOXINS

[75] Inventors: Jeroen Van Rie, Eeklo; Stefan Jansens, Gent; Marnix Peferoen, Nevele, all of Belgium

[73] Assignee: Plant Genetic Systems, N.V., Gent, Belgium

[21] Appl. No.: 295,060

[22] Filed: Aug. 26, 1994

[51] Int. Cl.$^6$ .............................. A01H 4/00; C12N 15/32; C07K 14/325

[52] U.S. Cl. .................. 800/205; 800/250; 800/DIG. 56; 514/12; 536/23.71; 435/172.3

[58] Field of Search ...................... 536/23.71; 800/205, 800/250, DIG. 56; 514/12; 435/69.1, 172.3

[56] References Cited

PUBLICATIONS

Perlak et al. (1993) Plant Molecular Biology vol. 22, pp. 313–321.

Adang et al (1993) Plant Molecular Biology, vol. 21, pp. 1131–1145.

Cunningham et al (1989) Science vol. 244, pp. 1081–1084.

Li et al. (1991) Nature vol. 353, pp. 815–821.

Widner et al (1990) Journal of Bacteriology, vol. 172, pp. 2826–2832.

*Primary Examiner*—Che S. Chereskin
*Attorney, Agent, or Firm*—Burns, Doane, Swecker & Mathis, LLP

[57] ABSTRACT

New modified Cry proteins, particularly modified CryIIIA proteins, having significantly altered toxicity, and DNA sequences encoding these proteins, are designed. Analysis of solvent-accessible amino acid positions in domain II of the CryIIIA protein by alanine-scanning mutagenesis identified individual amino acids involved in corn rootworm toxicity. Random replacement of these amino acids identifies modified proteins with improved toxicity. A combination of all or most thus identified improved amino acids in a single protein yields modified CryIIIA proteins with significantly improved toxicity. Particularly regions protruding from the Cry molecule and located at the apex of the Cry proteins, were identified as involved in toxicity.

21 Claims, No Drawings

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 1935 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Bacillus thuringiensis ( i x ) FEATURE:
( A ) NAME/KEY: CDS
( B ) LOCATION: 1..1933

( x i ) SEQUENCE DESCRIPTION: SEQ ID NO: 1:

```
ATG AAT CCG AAC AAT CGA AGT GAA CAT GAT ACA ATA AAA ACT ACT GAA        48
Met Asn Pro Asn Asn Arg Ser Glu His Asp Thr Ile Lys Thr Thr Glu
  1               5                  10                  15

AAT AAT GAG GTG CCA ACT AAC CAT GTT CAA TAT CCT TTA GCG GAA ACT        96
Asn Asn Glu Val Pro Thr Asn His Val Gln Tyr Pro Leu Ala Glu Thr
             20                  25                  30

CCA AAT CCA ACA CTA GAA GAT TTA AAT TAT AAA GAG TTT TTA AGA ATG       144
Pro Asn Pro Thr Leu Glu Asp Leu Asn Tyr Lys Glu Phe Leu Arg Met
         35                  40                  45

ACT GCA GAT AAT AAT ACG GAA GCA CTA GAT AGC TCT ACA ACA AAA GAT       192
Thr Ala Asp Asn Asn Thr Glu Ala Leu Asp Ser Ser Thr Thr Lys Asp
     50                  55                  60

GTC ATT CAA AAA GGC ATT TCC GTA GTA GGT GAT CTC CTA GGC GTA GTA       240
Val Ile Gln Lys Gly Ile Ser Val Val Gly Asp Leu Leu Gly Val Val
 65                  70                  75                  80

GGT TTC CCG TTT GGT GGA GCG CTT GTT TCG TTT TAT ACA AAC TTT TTA       288
Gly Phe Pro Phe Gly Gly Ala Leu Val Ser Phe Tyr Thr Asn Phe Leu
                 85                  90                  95

AAT ACT ATT TGG CCA AGT GAA GAC CCG TGG AAG GCT TTT ATG GAA CAA       336
Asn Thr Ile Trp Pro Ser Glu Asp Pro Trp Lys Ala Phe Met Glu Gln
            100                 105                 110

GTA GAA GCA TTG ATG GAT CAG AAA ATA GCT GAT TAT GCA AAA AAT AAA       384
Val Glu Ala Leu Met Asp Gln Lys Ile Ala Asp Tyr Ala Lys Asn Lys
        115                 120                 125

GCT CTT GCA GAG TTA CAG GGC CTT CAA AAT AAT GTC GAA GAT TAT GTG       432
Ala Leu Ala Glu Leu Gln Gly Leu Gln Asn Asn Val Glu Asp Tyr Val
    130                 135                 140

AGT GCA TTG AGT TCA TGG CAA AAA AAT CCT GTG AGT TCA CGA AAT CCA       480
Ser Ala Leu Ser Ser Trp Gln Lys Asn Pro Val Ser Ser Arg Asn Pro
145                 150                 155                 160

CAT AGC CAG GGG CGG ATA AGA GAG CTG TTT TCT CAA GCA GAA AGT CAT       528
His Ser Gln Gly Arg Ile Arg Glu Leu Phe Ser Gln Ala Glu Ser His
                165                 170                 175

TTT CGT AAT TCA ATG CCT TCG TTT GCA ATT TCT GGA TAC GAG GTT CTA       576
Phe Arg Asn Ser Met Pro Ser Phe Ala Ile Ser Gly Tyr Glu Val Leu
            180                 185                 190

TTT CTA ACA ACA TAT GCA CAA GCT GCC AAC ACA CAT TTA TTT TTA CTA       624
Phe Leu Thr Thr Tyr Ala Gln Ala Ala Asn Thr His Leu Phe Leu Leu
        195                 200                 205

AAA GAC GCT CAA ATT TAT GGA GAA GAA TGG GGA TAC GAA AAA GAA GAT       672
```

|     |     |     |     |     |     |     |     |     |     |     |     |     |     |     |      |
|-----|-----|-----|-----|-----|-----|-----|-----|-----|-----|-----|-----|-----|-----|-----|------|
| Lys | Asp | Ala | Gln | Ile | Tyr | Gly | Glu | Glu | Trp | Gly | Tyr | Glu | Lys | Glu | Asp  |
|     | 210 |     |     |     | 215 |     |     |     | 220 |     |     |     |     |     |      |

| ATT | GCT | GAA | TTT | TAT | AAA | AGA | CAA | CTA | AAA | CTT | ACG | CAA | GAA | TAT | ACT | 720 |
|-----|-----|-----|-----|-----|-----|-----|-----|-----|-----|-----|-----|-----|-----|-----|-----|-----|
| Ile | Ala | Glu | Phe | Tyr | Lys | Arg | Gln | Leu | Lys | Leu | Thr | Gln | Glu | Tyr | Thr |     |
| 225 |     |     |     |     | 230 |     |     |     | 235 |     |     |     |     |     | 240 |     |

| GAC | CAT | TGT | GTC | AAA | TGG | TAT | AAT | GTT | GGA | TTA | GAT | AAA | TTA | AGA | GGT | 768 |
|-----|-----|-----|-----|-----|-----|-----|-----|-----|-----|-----|-----|-----|-----|-----|-----|-----|
| Asp | His | Cys | Val | Lys | Trp | Tyr | Asn | Val | Gly | Leu | Asp | Lys | Leu | Arg | Gly |     |
|     |     |     |     | 245 |     |     |     |     | 250 |     |     |     |     | 255 |     |     |

| TCA | TCT | TAT | GAA | TCT | TGG | GTA | AAC | TTT | AAC | CGT | TAT | CGC | AGA | GAG | ATG | 816 |
|-----|-----|-----|-----|-----|-----|-----|-----|-----|-----|-----|-----|-----|-----|-----|-----|-----|
| Ser | Ser | Tyr | Glu | Ser | Trp | Val | Asn | Phe | Asn | Arg | Tyr | Arg | Arg | Glu | Met |     |
|     |     |     |     | 260 |     |     |     |     | 265 |     |     |     |     | 270 |     |     |

| ACA | TTA | ACA | GTA | TTA | GAT | TTA | ATT | GCA | CTA | TTT | CCA | TTG | TAT | GAT | GTT | 864 |
|-----|-----|-----|-----|-----|-----|-----|-----|-----|-----|-----|-----|-----|-----|-----|-----|-----|
| Thr | Leu | Thr | Val | Leu | Asp | Leu | Ile | Ala | Leu | Phe | Pro | Leu | Tyr | Asp | Val |     |
|     |     |     | 275 |     |     |     |     | 280 |     |     |     |     | 285 |     |     |     |

| CGG | CTA | TAC | CCA | AAA | GAA | GTT | AAA | ACC | GAA | TTA | ACA | AGA | GAC | GTT | TTA | 912 |
|-----|-----|-----|-----|-----|-----|-----|-----|-----|-----|-----|-----|-----|-----|-----|-----|-----|
| Arg | Leu | Tyr | Pro | Lys | Glu | Val | Lys | Thr | Glu | Leu | Thr | Arg | Asp | Val | Leu |     |
|     | 290 |     |     |     |     | 295 |     |     |     |     | 300 |     |     |     |     |     |

| ACA | GAT | CCA | ATT | GTC | GGA | GTC | AAC | AAC | CTT | AGG | GGC | TAT | GGA | ACA | ACC | 960 |
|-----|-----|-----|-----|-----|-----|-----|-----|-----|-----|-----|-----|-----|-----|-----|-----|-----|
| Thr | Asp | Pro | Ile | Val | Gly | Val | Asn | Asn | Leu | Arg | Gly | Tyr | Gly | Thr | Thr |     |
| 305 |     |     |     |     | 310 |     |     |     |     | 315 |     |     |     |     | 320 |     |

| TTC | TCT | AAT | ATA | GAA | AAT | TAT | ATT | CGA | AAA | CCA | CAT | CTA | TTT | GAC | TAT | 1008 |
|-----|-----|-----|-----|-----|-----|-----|-----|-----|-----|-----|-----|-----|-----|-----|-----|------|
| Phe | Ser | Asn | Ile | Glu | Asn | Tyr | Ile | Arg | Lys | Pro | His | Leu | Phe | Asp | Tyr |      |
|     |     |     |     | 325 |     |     |     |     | 330 |     |     |     |     | 335 |     |      |

| CTG | CAT | AGA | ATT | CAA | TTT | CAC | ACG | CGG | TTC | CAA | CCA | GGA | TAT | TAT | GGA | 1056 |
|-----|-----|-----|-----|-----|-----|-----|-----|-----|-----|-----|-----|-----|-----|-----|-----|------|
| Leu | His | Arg | Ile | Gln | Phe | His | Thr | Arg | Phe | Gln | Pro | Gly | Tyr | Tyr | Gly |      |
|     |     |     | 340 |     |     |     |     | 345 |     |     |     |     | 350 |     |     |      |

| AAT | GAC | TCT | TTC | AAT | TAT | TGG | TCC | GGT | AAT | TAT | GTT | TCA | ACT | AGA | CCA | 1104 |
|-----|-----|-----|-----|-----|-----|-----|-----|-----|-----|-----|-----|-----|-----|-----|-----|------|
| Asn | Asp | Ser | Phe | Asn | Tyr | Trp | Ser | Gly | Asn | Tyr | Val | Ser | Thr | Arg | Pro |      |
|     |     | 355 |     |     |     |     | 360 |     |     |     |     | 365 |     |     |     |      |

| AGC | ATA | GGA | TCA | AAT | GAT | ATA | ATC | ACA | TCT | CCA | TTC | TAT | GGA | AAT | AAA | 1152 |
|-----|-----|-----|-----|-----|-----|-----|-----|-----|-----|-----|-----|-----|-----|-----|-----|------|
| Ser | Ile | Gly | Ser | Asn | Asp | Ile | Ile | Thr | Ser | Pro | Phe | Tyr | Gly | Asn | Lys |      |
|     |     | 370 |     |     |     |     | 375 |     |     |     |     | 380 |     |     |     |      |

| TCC | AGT | GAA | CCT | GTA | CAA | AAT | TTA | GAA | TTT | AAT | GGA | GAA | AAA | GTC | TAT | 1200 |
|-----|-----|-----|-----|-----|-----|-----|-----|-----|-----|-----|-----|-----|-----|-----|-----|------|
| Ser | Ser | Glu | Pro | Val | Gln | Asn | Leu | Glu | Phe | Asn | Gly | Glu | Lys | Val | Tyr |      |
| 385 |     |     |     |     | 390 |     |     |     |     | 395 |     |     |     |     | 400 |      |

| AGA | GCC | GTA | GCA | AAT | ACA | AAT | CTT | GCG | GTC | TGG | CCG | TCC | GCT | GTA | TAT | 1248 |
|-----|-----|-----|-----|-----|-----|-----|-----|-----|-----|-----|-----|-----|-----|-----|-----|------|
| Arg | Ala | Val | Ala | Asn | Thr | Asn | Leu | Ala | Val | Trp | Pro | Ser | Ala | Val | Tyr |      |
|     |     |     |     | 405 |     |     |     |     | 410 |     |     |     |     | 415 |     |      |

| TCA | GGT | GTT | ACA | AAA | GTG | GAA | TTT | AGC | CAA | TAT | AAT | GAT | CAA | ACA | GAT | 1296 |
|-----|-----|-----|-----|-----|-----|-----|-----|-----|-----|-----|-----|-----|-----|-----|-----|------|
| Ser | Gly | Val | Thr | Lys | Val | Glu | Phe | Ser | Gln | Tyr | Asn | Asp | Gln | Thr | Asp |      |
|     |     |     | 420 |     |     |     |     | 425 |     |     |     |     | 430 |     |     |      |

| GAA | GCA | AGT | ACA | CAA | ACG | TAC | GAC | TCA | AAA | AGA | AAT | GTT | GGC | GCG | GTC | 1344 |
|-----|-----|-----|-----|-----|-----|-----|-----|-----|-----|-----|-----|-----|-----|-----|-----|------|
| Glu | Ala | Ser | Thr | Gln | Thr | Tyr | Asp | Ser | Lys | Arg | Asn | Val | Gly | Ala | Val |      |
|     |     | 435 |     |     |     |     | 440 |     |     |     |     | 445 |     |     |     |      |

| AGC | TGG | GAT | TCT | ATC | GAT | CAA | TTG | CCT | CCA | GAA | ACA | ACA | GAT | GAA | CCT | 1392 |
|-----|-----|-----|-----|-----|-----|-----|-----|-----|-----|-----|-----|-----|-----|-----|-----|------|
| Ser | Trp | Asp | Ser | Ile | Asp | Gln | Leu | Pro | Pro | Glu | Thr | Thr | Asp | Glu | Pro |      |
|     | 450 |     |     |     |     | 455 |     |     |     |     | 460 |     |     |     |     |      |

| CTA | GAA | AAG | GGA | TAT | AGC | CAT | CAA | CTC | AAT | TAT | GTA | ATG | TGC | TTT | TTA | 1440 |
|-----|-----|-----|-----|-----|-----|-----|-----|-----|-----|-----|-----|-----|-----|-----|-----|------|
| Leu | Glu | Lys | Gly | Tyr | Ser | His | Gln | Leu | Asn | Tyr | Val | Met | Cys | Phe | Leu |      |
| 465 |     |     |     |     | 470 |     |     |     |     | 475 |     |     |     |     | 480 |      |

| ATG | CAG | GGT | AGT | AGA | GGA | ACA | ATC | CCA | GTG | TTA | ACT | TGG | ACA | CAT | AAA | 1488 |
|-----|-----|-----|-----|-----|-----|-----|-----|-----|-----|-----|-----|-----|-----|-----|-----|------|
| Met | Gln | Gly | Ser | Arg | Gly | Thr | Ile | Pro | Val | Leu | Thr | Trp | Thr | His | Lys |      |
|     |     |     |     | 485 |     |     |     |     | 490 |     |     |     |     | 495 |     |      |

| AGT | GTA | GAC | TTT | TTT | AAC | ATG | ATT | GAT | TCG | AAA | AAA | ATT | ACA | CAA | CTT | 1536 |
|-----|-----|-----|-----|-----|-----|-----|-----|-----|-----|-----|-----|-----|-----|-----|-----|------|
| Ser | Val | Asp | Phe | Phe | Asn | Met | Ile | Asp | Ser | Lys | Lys | Ile | Thr | Gln | Leu |      |
|     |     |     | 500 |     |     |     |     | 505 |     |     |     |     | 510 |     |     |      |

| CCG | TTA | GTA | AAG | GCA | TAT | AAG | TTA | CAA | TCT | GGT | GCT | TCC | GTT | GTC | GCA | 1584 |
|-----|-----|-----|-----|-----|-----|-----|-----|-----|-----|-----|-----|-----|-----|-----|-----|------|
| Pro | Leu | Val | Lys | Ala | Tyr | Lys | Leu | Gln | Ser | Gly | Ala | Ser | Val | Val | Ala |      |
|     |     | 515 |     |     |     |     | 520 |     |     |     |     | 525 |     |     |     |      |

| GGT | CCT | AGG | TTT | ACA | GGA | GGA | GAT | ATC | ATT | CAA | TGC | ACA | GAA | AAT | GGA | 1632 |

```
Gly Pro Arg Phe Thr Gly Gly Asp Ile Ile Gln Cys Thr Glu Asn Gly
    530                 535                 540

AGT GCG GCA ACT ATT TAC GTT ACA CCG GAT GTG TCG TAC TCT CAA AAA    1680
Ser Ala Ala Thr Ile Tyr Val Thr Pro Asp Val Ser Tyr Ser Gln Lys
545             550                 555                 560

TAT CGA GCT AGA ATT CAT TAT GCT TCT ACA TCT CAG ATA ACA TTT ACA    1728
Tyr Arg Ala Arg Ile His Tyr Ala Ser Thr Ser Gln Ile Thr Phe Thr
                565             570                 575

CTC AGT TTA GAC GGG GCA CCA TTT AAT CAA TAC TAT TTC GAT AAA ACG    1776
Leu Ser Leu Asp Gly Ala Pro Phe Asn Gln Tyr Tyr Phe Asp Lys Thr
            580             585                 590

ATA AAT AAA GGA GAC ACA TTA ACG TAT AAT TCA TTT AAT TTA GCA AGT    1824
Ile Asn Lys Gly Asp Thr Leu Thr Tyr Asn Ser Phe Asn Leu Ala Ser
        595                 600             605

TTC AGC ACA CCA TTC GAA TTA TCA GGG AAT AAC TTA CAA ATA GGC GTC    1872
Phe Ser Thr Pro Phe Glu Leu Ser Gly Asn Asn Leu Gln Ile Gly Val
    610                 615                 620

ACA GGA TTA AGT GCT GGA GAT AAA GTT TAT ATA GAC AAA ATT GAA TTT    1920
Thr Gly Leu Ser Ala Gly Asp Lys Val Tyr Ile Asp Lys Ile Glu Phe
625             630                 635                 640

ATT CCA GTG AAT T AA                                               1935
Ile Pro Val Asn
```

( 2 ) INFORMATION FOR SEQ ID NO: 2:

( i ) SEQUENCE CHARACTERISTICS:
        ( A ) LENGTH: 644 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met Asn Pro Asn Asn Arg Ser Glu His Asp Thr Ile Lys Thr Thr Glu
 1               5                  10                  15

Asn Asn Glu Val Pro Thr Asn His Val Gln Tyr Pro Leu Ala Glu Thr
                20                  25                  30

Pro Asn Pro Thr Leu Glu Asp Leu Asn Tyr Lys Glu Phe Leu Arg Met
            35                  40                  45

Thr Ala Asp Asn Asn Thr Glu Ala Leu Asp Ser Ser Thr Thr Lys Asp
        50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
                100                 105                 110

Val Glu Ala Leu Met Asp Gln Lys Ile Ala Asp Tyr Ala Lys Asn Lys
            115                 120                 125

Ala Leu Ala Glu Leu Gln Gly Leu Gln Asn Asn Val Glu Asp Tyr Val
        130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
                180                 185                 190

Phe Leu Thr Thr Tyr Ala Gln Ala Ala Asn Thr His Leu Phe Leu Leu
            195                 200                 205
```

-continued

| | | | | | | | | | | | | | |
|---|---|---|---|---|---|---|---|---|---|---|---|---|---|
|Lys|Asp 210|Ala|Gln|Ile|Tyr 215|Gly|Glu|Trp|Gly 220|Tyr|Glu|Lys|Glu|Asp|
|Ile 225|Ala|Glu|Phe|Tyr|Lys 230|Arg|Gln|Leu|Lys|Leu 235|Thr|Gln|Glu|Tyr|Thr 240|
|Asp|His|Cys|Val|Lys 245|Trp|Tyr|Asn|Val|Gly 250|Leu|Asp|Lys|Leu|Arg 255|Gly|
|Ser|Ser|Tyr|Glu 260|Ser|Trp|Val|Asn|Phe 265|Asn|Arg|Tyr|Arg 270|Arg|Glu|Met|
|Thr|Leu|Thr 275|Val|Leu|Asp|Leu|Ile 280|Ala|Leu|Phe|Pro|Leu 285|Tyr|Asp|Val|
|Arg|Leu 290|Tyr|Pro|Lys|Glu|Val 295|Lys|Thr|Glu|Leu|Thr 300|Arg|Asp|Val|Leu|
|Thr 305|Asp|Pro|Ile|Val|Gly 310|Val|Asn|Asn|Leu|Arg 315|Gly|Tyr|Gly|Thr|Thr 320|
|Phe|Ser|Asn|Ile|Glu 325|Asn|Tyr|Ile|Arg|Lys 330|Pro|His|Leu|Phe|Asp 335|Tyr|
|Leu|His|Arg|Ile 340|Gln|Phe|His|Thr|Arg 345|Phe|Gln|Pro|Gly|Tyr 350|Tyr|Gly|
|Asn|Asp|Ser 355|Phe|Asn|Tyr|Trp|Ser 360|Gly|Asn|Tyr|Val|Ser 365|Thr|Arg|Pro|
|Ser|Ile 370|Gly|Ser|Asn|Asp|Ile 375|Ile|Thr|Ser|Pro|Phe 380|Tyr|Gly|Asn|Lys|
|Ser 385|Ser|Glu|Pro|Val|Gln 390|Asn|Leu|Glu|Phe|Asn 395|Gly|Glu|Lys|Val|Tyr 400|
|Arg|Ala|Val|Ala|Asn 405|Thr|Asn|Leu|Ala|Val 410|Trp|Pro|Ser|Ala|Val 415|Tyr|
|Ser|Gly|Val|Thr 420|Lys|Val|Glu|Phe|Ser 425|Gln|Tyr|Asn|Asp|Gln 430|Thr|Asp|
|Glu|Ala|Ser|Thr 435|Gln|Thr|Tyr|Asp|Ser 440|Lys|Arg|Asn|Val|Gly 445|Ala|Val|
|Ser|Trp 450|Asp|Ser|Ile|Asp|Gln 455|Leu|Pro|Pro|Glu|Thr 460|Thr|Asp|Glu|Pro|
|Leu 465|Glu|Lys|Gly|Tyr|Ser 470|His|Gln|Leu|Asn|Tyr 475|Val|Met|Cys|Phe|Leu 480|
|Met|Gln|Gly|Ser|Arg 485|Gly|Thr|Ile|Pro|Val 490|Leu|Thr|Trp|Thr|His 495|Lys|
|Ser|Val|Asp|Phe 500|Phe|Asn|Met|Ile|Asp 505|Ser|Lys|Lys|Ile|Thr 510|Gln|Leu|
| |Pro|Leu|Val|Lys 515|Ala|Tyr|Lys|Leu|Gln 520|Ser|Gly|Ala|Ser|Val 525|Val|Ala|
|Gly|Pro 530|Arg|Phe|Thr|Gly|Gly 535|Asp|Ile|Ile|Gln|Cys 540|Thr|Glu|Asn|Gly|
|Ser 545|Ala|Ala|Thr|Ile|Tyr 550|Val|Thr|Pro|Asp|Val 555|Ser|Tyr|Ser|Gln|Lys 560|
|Tyr|Arg|Ala|Arg|Ile 565|His|Tyr|Ala|Ser|Thr 570|Ser|Gln|Ile|Thr|Phe 575|Thr|
|Leu|Ser|Leu|Asp 580|Gly|Ala|Pro|Phe|Asn 585|Gln|Tyr|Tyr|Phe|Asp 590|Lys|Thr|
|Ile|Asn|Lys 595|Gly|Asp|Thr|Leu|Thr 600|Tyr|Asn|Ser|Phe|Asn 605|Leu|Ala|Ser|
|Phe|Ser 610|Thr|Pro|Phe|Glu|Leu 615|Ser|Gly|Asn|Asn|Leu 620|Gln|Ile|Gly|Val|
|Thr|Gly|Leu|Ser|Ala|Gly|Asp|Lys|Val|Tyr|Ile|Asp|Lys|Ile|Glu|Phe|

|   625          |   630          |   635          |   640          |

Ile Pro Val Asn ( 2 ) INFORMATION FOR SEQ ID NO: 3:

( i ) SEQUENCE CHARACTERISTICS:
        ( A ) LENGTH: 1957 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: YES ( i i i ) ANTI-SENSE: NO ( i x ) FEATURE:
        ( A ) NAME/KEY: CDS
        ( B ) LOCATION: 13..1947

( x i ) SEQUENCE DESCRIPTION: SEQ ID NO: 3:

| | | | | | |
|---|---|---|---|---|---|
| GGTACCAAAA | CCATGGCTAA | CCCCAACAAC | CGCAGCGAGC | ACGACACCAT | CAAGACCACC | 60 |
| GAGAACAACG | AGGTGCCCAC | CAACCACGTG | CAGTACCCCC | TGGCCGAGAC | CCCAAACCCC | 120 |
| ACCCTGGAGG | ACCTGAACTA | CAAGGAGTTC | CTGCGCATGA | CCGCCGACAA | CAACACCGAG | 180 |
| GCCCTGGACA | GCAGCACCAC | CAAGGACGTG | ATCCAGAAGG | GCATCAGCGT | GGTGGGCGAC | 240 |
| CTGCTGGGCG | TGGTGGGCTT | CCCCTTCGGT | GGTGCCCTGG | TGAGCTTCTA | CACCAACTTC | 300 |
| CTGAACACCA | TCTGGCCCAG | CGAGGACCCC | TGGAAGGCCT | TCATGGAGCA | GGTGGAGGCC | 360 |
| CTGATGGACC | AGAAGATCGC | CGACTACGCC | AAGAACAAGG | CCCTGGCCGA | GCTGCAGGGC | 420 |
| CTGCAGAACA | ACGTGGAGGA | CTACGTGAGC | GCCCTGAGCA | GCTGGCAGAA | GAACCCCGTG | 480 |
| AGCAGCCGCA | ACCCCACAG | CCAGGGTCGC | ATCCGCGAGC | TGTTCAGCCA | GGCCGAGAGC | 540 |
| CACTTCCGCA | ACAGCATGCC | CAGCTTCGCC | ATCAGCGGCT | ACGAGGTGCT | GTTCCTGACC | 600 |
| ACCTACGCCC | AGGCTGCCAA | CACCCACCTG | TTCCTGCTGA | GGACGCCCA | GATCTACGGC | 660 |
| GAGGAGTGGG | GCTACGAGAA | GGAGGACATC | GCCGAGTTCT | ACAAGCGCCA | GCTGAAGCTG | 720 |
| ACCCAGGAGT | ACACCGACCA | CTGCGTGAAG | TGGTACAACG | TGGGCCTGGA | CAAGCTGAGG | 780 |
| GGCAGCAGCT | ACGAGAGCTG | GGTGAACTTC | AACCGCTACC | GCAGGGAGAT | GACCCTGACC | 840 |
| GTGCTGGACC | TGATCGCCCT | GTTCCCCCTG | TACGACGTGC | GCCTGTACCC | CAAGGAGGTG | 900 |
| AAGACCGAGC | TGACCCGCGA | CGTGCTGACC | GACCCCATCG | TGGGCGTGAA | CAACCTGAGG | 960 |
| GGCTACGGCA | CCACCTTCAG | CAACATCGAG | AACTACATCC | GCAAGCCCCA | CCTGTTCGAC | 1020 |
| TACCTGCACC | GCATCCAGTT | CCACACCCGC | NNNNNNNNN | NNNNNTACGG | CAACGACAGC | 1080 |
| TTCAACTACT | GGAGCGGCAA | CTACGTGAGC | ACTCGCCCCA | GCATCGGCAG | CAACGACATC | 1140 |
| ATCACCAGCC | CATTCTATGG | CAACAAGAGC | AGCGAGCCCG | TGCAGAACCT | GGAGTTCAAC | 1200 |
| GGCGAGAAGG | TGTACAGGGC | CGTGGCCAAC | ACCAACCTTG | CCGTGNNNNN | NAGCGCCGTG | 1260 |
| NNNAGCGGCG | TGACCAAGGT | GGAGTTCAGC | CAGTACAATG | ATCAGACCGA | CGAGGCCAGC | 1320 |
| ACCCAGACCT | ACGACAGCNN | NCGCAACGTG | GGCGCTGTGA | GCTGGACAG | CATCGACCAG | 1380 |
| CTGCCTCCCG | AGACCACCGA | CGAGCCCCTG | GAGAAGGGCT | ACAGCCACCA | GCTGAACTAC | 1440 |
| GTGATGTGCT | TCCTGATGCA | GGGCAGCAGG | GGCACCATCC | CAGTGCTGAC | CTGGACCCAC | 1500 |
| AAGAGCGTGG | ACTTCTTCAA | CATGATCGAC | AGCAAGAAGA | TCACCCAGCT | GCCCCTGGTG | 1560 |
| AAGGCCTACA | AGCTGCAGAG | CGGTGCCTCC | GTGGTTGCCG | GCCACGCTT | CACCGGTGGC | 1620 |
| GACATCATCC | AGTGCACCGA | GAACGGCAGC | GCTGCCACCA | TCTACGTGAC | CCCCGACGTG | 1680 |

```
AGCTACAGCC AGAAGTACCG CGCTCGCATC CACTACGCCA GCACCAGCCA GATCACCTTC    1740

ACCCTGAGCC TGGATGGGGC CCCATTCAAC CAGTACTACT TCGACAAGAC CATCAACAAG    1800

GGCGACACCC TGACCTACAA CAGCTTCAAC CTGGCCAGCT TCAGCACCCC CTTCGAGCTG    1860

AGCGGCAACA ACCTGCAGAT CGGCGTGACC GGCCTGAGCG CTGGCGACAA GGTGTACATC    1920

GACAAGATCG AGTTCATCCC CGTGAACTGA GGCTAGC                             1957
```

( 2 ) INFORMATION FOR SEQ ID NO: 4:

( i ) SEQUENCE CHARACTERISTICS:
        ( A ) LENGTH: 645 amino acids
        ( B ) TYPE: amino acid
        ( D ) TOPOLOGY: linear ( i i ) MOLECULE TYPE: protein ( i i i ) HYPOTHETICAL: YES ( x i ) SEQUENCE DESCRIPTION: SEQ ID NO: 4:

```
Met Ala Asn Pro Asn Asn Arg Ser Glu His Asp Thr Ile Lys Thr Thr
 1               5                  10                  15

Glu Asn Asn Glu Val Pro Thr Asn His Val Gln Tyr Pro Leu Ala Glu
            20                  25                  30

Thr Pro Asn Pro Thr Leu Glu Asp Leu Asn Tyr Lys Glu Phe Leu Arg
        35                  40                  45

Met Thr Ala Asp Asn Asn Thr Glu Ala Leu Asp Ser Ser Thr Thr Lys
    50                  55                  60

Asp Val Ile Gln Lys Gly Ile Ser Val Val Gly Asp Leu Leu Gly Val
65                  70                  75                  80

Val Gly Phe Pro Phe Gly Gly Ala Leu Val Ser Phe Tyr Thr Asn Phe
                85                  90                  95

Leu Asn Thr Ile Trp Pro Ser Glu Asp Pro Trp Lys Ala Phe Met Glu
            100                 105                 110

Gln Val Glu Ala Leu Met Asp Gln Lys Ile Ala Asp Tyr Ala Lys Asn
        115                 120                 125

Lys Ala Leu Ala Glu Leu Gln Gly Leu Gln Asn Asn Val Glu Asp Tyr
    130                 135                 140

Val Ser Ala Leu Ser Ser Trp Gln Lys Asn Pro Val Ser Ser Arg Asn
145                 150                 155                 160

Pro His Ser Gln Gly Arg Ile Arg Glu Leu Phe Ser Gln Ala Glu Ser
                165                 170                 175

His Phe Arg Asn Ser Met Pro Ser Phe Ala Ile Ser Gly Tyr Glu Val
            180                 185                 190

Leu Phe Leu Thr Thr Tyr Ala Gln Ala Ala Asn Thr His Leu Phe Leu
        195                 200                 205

Leu Lys Asp Ala Gln Ile Tyr Gly Glu Glu Trp Gly Tyr Glu Lys Glu
    210                 215                 220

Asp Ile Ala Glu Phe Tyr Lys Arg Gln Leu Lys Leu Thr Gln Glu Tyr
225                 230                 235                 240

Thr Asp His Cys Val Lys Trp Tyr Asn Val Gly Leu Asp Lys Leu Arg
                245                 250                 255

Gly Ser Ser Tyr Glu Ser Trp Val Asn Phe Asn Arg Tyr Arg Arg Glu
            260                 265                 270

Met Thr Leu Thr Val Leu Asp Leu Ile Ala Leu Phe Pro Leu Tyr Asp
        275                 280                 285

Val Arg Leu Tyr Pro Lys Glu Val Lys Thr Glu Leu Thr Arg Asp Val
```

|   |   |   |   |   | 290 |   |   |   |   |   |   | 295 |   |   |   |   |   | 300 |   |
|---|---|---|---|---|---|---|---|---|---|---|---|---|---|---|---|---|---|---|---|
| Leu | Thr | Asp | Pro | Ile | Val | Gly | Val | Asn | Asn | Leu | Arg | Gly | Tyr | Gly | Thr |
| 305 | | | | | 310 | | | | | 315 | | | | | 320 |
| Thr | Phe | Ser | Asn | Ile | Glu | Asn | Tyr | Ile | Arg | Lys | Pro | His | Leu | Phe | Asp |
| | | | | 325 | | | | | 330 | | | | | 335 | |
| Tyr | Leu | His | Arg | Ile | Gln | Phe | His | Thr | Arg | Xaa | Xaa | Xaa | Xaa | Xaa | Tyr |
| | | | 340 | | | | | 345 | | | | | 350 | | |
| Gly | Asn | Asp | Ser | Phe | Asn | Tyr | Trp | Ser | Gly | Asn | Tyr | Val | Ser | Thr | Arg |
| | | 355 | | | | | 360 | | | | | 365 | | | |
| Pro | Ser | Ile | Gly | Ser | Asn | Asp | Ile | Ile | Thr | Ser | Pro | Phe | Tyr | Gly | Asn |
| | 370 | | | | | 375 | | | | | 380 | | | | |
| Lys | Ser | Ser | Glu | Pro | Val | Gln | Asn | Leu | Glu | Phe | Asn | Gly | Glu | Lys | Val |
| 385 | | | | | 390 | | | | | 395 | | | | | 400 |
| Tyr | Arg | Ala | Val | Ala | Asn | Thr | Asn | Leu | Ala | Val | Xaa | Xaa | Ser | Ala | Val |
| | | | | 405 | | | | | 410 | | | | | 415 | |
| Xaa | Ser | Gly | Val | Thr | Lys | Val | Glu | Phe | Ser | Gln | Tyr | Asn | Asp | Gln | Thr |
| | | | 420 | | | | | 425 | | | | | 430 | | |
| Asp | Glu | Ala | Ser | Thr | Gln | Thr | Tyr | Asp | Ser | Xaa | Arg | Asn | Val | Gly | Ala |
| | | 435 | | | | | 440 | | | | | 445 | | | |
| Val | Ser | Trp | Asp | Ser | Ile | Asp | Gln | Leu | Pro | Pro | Glu | Thr | Thr | Asp | Glu |
| | 450 | | | | | 455 | | | | | 460 | | | | |
| Pro | Leu | Glu | Lys | Gly | Tyr | Ser | His | Gln | Leu | Asn | Tyr | Val | Met | Cys | Phe |
| 465 | | | | | 470 | | | | | 475 | | | | | 480 |
| Leu | Met | Gln | Gly | Ser | Arg | Gly | Thr | Ile | Pro | Val | Leu | Thr | Trp | Thr | His |
| | | | | 485 | | | | | 490 | | | | | 495 | |
| Lys | Ser | Val | Asp | Phe | Phe | Asn | Met | Ile | Asp | Ser | Lys | Lys | Ile | Thr | Gln |
| | | | 500 | | | | | 505 | | | | | 510 | | |
| Leu | Pro | Leu | Val | Lys | Ala | Tyr | Lys | Leu | Gln | Ser | Gly | Ala | Ser | Val | Val |
| | | 515 | | | | | 520 | | | | | 525 | | | |
| Ala | Gly | Pro | Arg | Phe | Thr | Gly | Gly | Asp | Ile | Ile | Gln | Cys | Thr | Glu | Asn |
| | 530 | | | | | 535 | | | | | 540 | | | | |
| Gly | Ser | Ala | Ala | Thr | Ile | Tyr | Val | Thr | Pro | Asp | Val | Ser | Tyr | Ser | Gln |
| 545 | | | | | 550 | | | | | 555 | | | | | 560 |
| Lys | Tyr | Arg | Ala | Arg | Ile | His | Tyr | Ala | Ser | Thr | Ser | Gln | Ile | Thr | Phe |
| | | | | 565 | | | | | 570 | | | | | 575 | |
| Thr | Leu | Ser | Leu | Asp | Gly | Ala | Pro | Phe | Asn | Gln | Tyr | Tyr | Phe | Asp | Lys |
| | | | 580 | | | | | 585 | | | | | 590 | | |
| Thr | Ile | Asn | Lys | Gly | Asp | Thr | Leu | Thr | Tyr | Asn | Ser | Phe | Asn | Leu | Ala |
| | | 595 | | | | | 600 | | | | | 605 | | | |
| Ser | Phe | Ser | Thr | Pro | Phe | Glu | Leu | Ser | Gly | Asn | Asn | Leu | Gln | Ile | Gly |
| | 610 | | | | | 615 | | | | | 620 | | | | |
| Val | Thr | Gly | Leu | Ser | Ala | Gly | Asp | Lys | Val | Tyr | Ile | Asp | Lys | Ile | Glu |
| 625 | | | | | 630 | | | | | 635 | | | | | 640 |
| Phe | Ile | Pro | Val | Asn |
| | | | | 645 |

DIABROTICA TOXINS

INTRODUCTION

The present invention provides new proteins for combatting insects, particularly Coleoptera, preferably corn rootworms. In accordance with this invention, single amino acid residues in a CryIII protein were identified as involved in corn rootworm toxicity. Further in accordance with this invention are provided modified CryIII proteins, particularly modified CryIIIA proteins, with altered toxicity, preferably increased toxicity, towards Coleoptera, particularly corn rootworms, specifically *Diabrotica virgifera virgifera*, and DNA sequences encoding these proteins. Plants, preferably corn plants, are protected from insect damage by expressing a chimeric gene encoding a modified CryIII protein with improved coleopteran toxicity in their cells, particularly by expressing a chimeric gene encoding a modified CryIIIA protein with improved corn rootworm toxicity in the cells of a corn plant.

BACKGROUND OF THE INVENTION

Corn Rootworms

Among the corn rootworms are found some of the most destructive insect pests. The corn rootworms *Diabrotica virgifera virgifera* (western corn rootworm) and *Diabrotica barberi* (northern corn rootworm) are considered the most serious inset pests of corn in the major corn-producing states of the USA and Canada (Levine and Oloumi-Sadeghi, 1991, Annu. Rev. Entomol. 36, 229–55). The larvae feed on corn roots, thus causing direct damage to corn growth and corn yields. Extensive root damage makes plants also more susceptible to lodging. Adults are strong flyers and feed on corn silks and leaves. Furthermore, these insects are also vectors of diseases such as the maize chlorotic mottle virus. Costs for soil insecticides to control larval damage to the root systems of corn and aerial sprays to reduce beetle damage to corn silks, when combined with crop losses, are estimated to reach up to 1 billion US dollars annually (Metcalf, 1986, Foreword in "Methods for the study of Pest Diabrotica", pp. vii–xv, eds. Krysan J. L. and Miller, T. A., Springer Verlag, New York). Besides corn, Diabrotica species also cause major damage to vegetable plants, mainly to plants of the Cucurbitaceae.

Although the CryIIIA protein was found to be very toxic to the Colorado potato beetle, the protein has been found to have weak, if any, toxicity to Diabrotica spp. (Johnson et al., 1993, J. Econ. Entomol. 86, 330). According to Slaney et al. (1992, Insect Biochem. Molec. Biol. 22, 9–18) the toxin encoded by the cryIIIA gene was found to be at least 2000 times less effective to *Diabrotica undecimpunctata howardi* larvae than to the Colorado potato beetle, *Leptinotarsa decemlineata*. Some mortality of crude extracts comprising the *Bt tenebrionis* toxin, although at undetermined concentration, to western corn rootworm has been reported (EP 0318143).

B. thuringiensis: Mode of Action and Structure-Function Analysis

*B. thuringiensis* (*Bt*) is a gram-positive bacterium which produces endogenous crystals upon sporulation. The crystals are composed of proteins, termed insecticidal crystal proteins (furtheron named "ICPs" or "Cry proteins"), that are specifically toxic against insect larvae. Three different *Bt* pathotypes have been described: pathotype A that is active against Lepidoptera, e.g. caterpillars; pathotype B that is active against certain Diptera, e.g. mosquitoes and black flies; and pathotype C that is active against Coleoptera, e.g. beetles (Ellar et al., 1986, In "Fundamental and Applied aspects of Invertebrate Pathology", ed. Samson, R. A., Vlak). Recently, *Bt* strains toxic to some other invertebrate species have been found (Feitelson, 1993, In *Advanced Engineered Pesticides*, ed. L. Kim, pp.63–71, Marcel Dekker, Inc., N.Y.; Koziel et al., 1993, Biotechn. and Genet. Engin. Revs. 11, 171–228). *Bt* strains, whose crystals are toxic to Coleoptera, have been described as *Bt tenebrionis* (U.S. Pat. No. 4,766,203; European patent publication ("EP") 0213818; U.S. Pat. No. 4,771,131), *Bt san diego* (EP 0238311) and BTS1 (EP 0305275). Subsequently, other coleopteran-active strains have been isolated (e.g. PCT patent publications WO 91/00791, WO 90/09445). The *Bt tenebrionis* strain, carrying the Coleopteran-active cryIIIA gene, has been reported to kill a variety of Coleoptera (Keller and Langenbruch, 1993; In: *Bacillus thuringiensis, An Environmental Biopesticide: Theory and Practice*, eds. Entwistle, P. F., Cory, J. S., Bailey, M. J. and Higgs, S.; John Wiley and Sons; New York; pp.171–191).

Most studies on the mode of action of *Bacillus thuringiensis* toxins have focused on lepidopteran-specific CryI ICPs. The following picture has emerged from these studies (Gill et al., 1992, Annu. Rev. Entomol. 37, 615–36; Knowles, 1993, BioEssays, 15, 469–476). Following ingestion of the crystals by a susceptible insect, they are dissolved in the alkaline reducing environment of the inset midgut lumen. The liberated proteins, the protoxins, are then proteolytically processed by insect midgut proteases to a protease-resistant fragment. This active fragment, the toxin, then passes through the peritrophic membrane and binds to specific receptors located on the brush border membrane of gut epithelial cells. Subsequent to binding, the toxin or part thereof inserts in the membrane resulting in the formation of pores. These pores lead to colloid osmotic swelling and ultimately lysis of the midgut cells, causing death of the insect.

In the case of CryIIIA, it is not clear if proteolytic processing occurs in vivo. This ICP has an in vitro solubility profile that differs significantly from that of CryI ICPs (Koller et al, 1992, Biochem. Biophys. Res. Commun. 184, 692–699). Binding experiments using brush border membrane vesicles from *Leptinotarsa decemlineata* indicated that the affinity of CryIIIA for midgut receptors in this species is about 1000 fold lower than the affinity calculated for most CryI proteins binding to brush border membrane vesicles of Lepidoptera (Slaney et al., 1992, supra). Channel formation in planar lipid bilayers has been demonstrated for CryIIIA (Slatin et al., 1990, Bioch. biophys. res. commun., 169, 765–772).

Most binding studies have demonstrated that receptor binding is a crucial step in the mode of action of ICPs (Hofmann et al., 1988, 173, 85–91; Hofmann et al., 1988, Proc. Natl. Acad. Sci. USA, 85, 7844–7848; Van Rie et al., 1990, Appl. Environm. Microbiol. 56, 1378–85). Indeed, most studies show a positive correlation between the biological activity of ICPs and their ability to bind to brush border membrane vesicles of insects (Gill et al., 1992, Annu. Rev. Entomol. 37, 615–636). However, Wolfersberger et al (1990, Experientia, 46, 475–477) demonstrated an inverse correlation between toxicity and binding for two ICPs in *Lymantria dispar*. Therefore, a straight correlation between toxicity and toxin binding, according to either receptor affinity or receptor concentration, may not always be a generally applicable concept (Gill et al., 1992, supra).

Recently, the three dimensional structure of one ICP, CryIIIA, has been solved (Li et al., 1991, Nature 353, 815–21). The protein has three structural domains: the N-terminal domain I consists of 7 alpha helices, domain II contains three beta-sheets and the C-terminal domain III is a beta-sandwich. Based on this structure, a hypothesis has been formulated regarding the structure-function relationships of ICPs. According to the authors, it would seem that the bundle of long, hydrophobic and amphipathic helices (domain I) is equipped for pore formation in the insect membrane, and regions of the three-sheet domain (domain II) are probably responsible for receptor binding (Li et al, 1991, supra). The function of domain III is less clear. When different ICP amino acid sequences are aligned, five conserved sequence blocks are evident (Höfte & Whiteley, 1989, Microbiol. Revs. 53, 242–255). In CryIIIA, these conserved blocks are all located in the interior of a structural domain or at the interface between domains. The high degree of conservation of these internal residues implies that homologous proteins would adopt a similar fold (Li et al., 1991, supra).

Data from Ahmad et al. (1991, FEMS Microbiol. Lett. 68, 97–104); Wu et al. (1992, J. Biol. Chem. 267, 2311–2317) and Gazit et al. (1993, Biochemistry 32, 3429–3436) provide evidence for the function of domain I of ICPs as a pore formation unit.

Different sets of hybrid ICP genes have been constructed through exchange of gene fragments between ICP genes, encoding ICPs with different insect specificities. The hybrid ICPs were tested in bioassays in order to located the specificity-determining region in the parental ICPs (Ge et al., 1989, Proc. Natl. Acad. Sci. USA 86, 4037–4041; Schnepf et al., 1990, J. Biol. Chem. 265, 20923–30; Widner and Whiteley, 1990, J. Bacteriol. 172, 2826–2832; Ge et al, 1991, J. Biol. Chem., 266, 17954–17958). The genetically identified specificity-determining regions can be mapped to equivalent positions in the CryIIIA structure, and these fall mainly in domain II (Li et al., 1991, supra). From studies with hybrid CryIA proteins, Lee et al. (1992, J. Biol. Chem., 267, 3115–3121) concluded that the *B. mori* receptor-binding region on the CryIAa toxin was the same as the previously-determined *B. mori* specificity-determining region of this molecule (i.e. amino acids 332–450). Furthermore, deletions and alanine substitutions in the CryIAa protoxin at a position supposed to be at or near the second loop of domain II significantly decreased toxicity and receptor binding ability (Lu et al., 1993, XXVIth Annual meeting of the Society for Invertebrate Pathology, Asheville, USA, Conference book, page 31, Abstract 17). Smith and Ellar (1992, XXVth Annual meeting of the Society for Invertebrate Pathology, Heidelberg, Germany, Conference book, page 111, abstract 68) observed dramatic effects on toxicity towards in vitro insect cell cultures with mutant CryIC proteins, differing in the amino acid sequence of the predicted loop regions. They formulated the hypothesis that it should be possible to map the putative receptor binding domain of this toxin and eventually generate toxins with increased potency. In some cases however, a contribution to specificity and binding from domain III of the Cry toxin could not be excluded (Schnepf et al., 1990, supra; Ge et al., 1991, supra). Furthermore, a recent study using hybrid ICPs constructed by exchanging gene fragments between cryIC and cryIE, has indicated that domain II of CryIC is not sufficient to confer the high activity of this protein towards *Spodoptera exigua* and *Mamestra brassicae* (Bosch et al., 1993, Seventh International Conference on Bacillus, Institut Pasteur, July 18–23, Abstracts of lectures, p. L6). Site-directed mutagenesis experiments on CryIA(c) indicated that certain amino acids in domain I are important for receptor binding (Wu et al., 1992, supra).

Also, changes outside the 60 kD toxin region of the *Bt* protoxin were found to influence toxicity. It was suggested that this may be related to the activation processes in the gut juice (Nakamura et al., 1990, Agric. Biol. Chem. 54, 715–24).

Visser et al. (1993, in "*Bacillus thuringiensis*, an Environmental Biopesticide: Theory and Practice", pp.71–88, eds.: Entwistle, P. F., Cory, J. S., Bailey, M. J., and Higgs, S., John Wiley & Sons, N.Y.) reviewed the domain-function studies with *Bt* ICPs and concluded that in general, the function of essential stretches of the toxic fragment of *Bt* ICPs is unknown. From studies of mutant proteins, it was found that several amino acid residues from different regions of the toxic fragment, either conserved, or variable, were shown to affect toxic activity. These studies have been performed with CryI and CryII proteins. In the case of CryIIIA, no experimental data are available regarding the location of the receptor binding region.

BRIEF SUMMARY OF THE INVENTION

This invention provides a DNA sequence encoding a modified CryIII protein having altered toxicity to Coleopteran insects, particularly corn rootworms. By changing amino acids on positions, identified as involved in toxicity, in accordance with this invention, a CryIII protein having significantly higher corn rootworm toxicity, particularly against *Diabrotica virgifera virgifera*, is designed. Also, in accordance with this invention, a CryIII protein having altered corn rootworm toxicity is provided, by changing amino acids in the loops and beta-strands protruding from domain II of the protein and folded towards or located at the molecular apex of the molecule. In a preferred embodiment of this invention, a DNA sequence encoding a modified CryIIIA protein with altered, preferably increased, corn rootworm, preferably western corn rootworm, toxicity, is provided. This modified CryIIIA protein is preferably made by changing at least one of the amino acids of the protruding regions folded towards or located at, preferably located at, the apex of the CryIIIA molecule, particularly by replacing at least one of the amino acids at positions 346, 347, 348, 349, 350, 411, 412, 416 or 442 of the CryIIIA protein of SEQ ID No. 2 by another amino acid, more preferably by changing at least one of the amino acids at positions 349, 350, 411, 412, and 416 of the CryIIIA protein of SEQ ID no 2.

In another preferred embodiment of this invention, a plant transformed with a DNA sequence encoding a new modified CryIII protein is provided, so that the plant acquires increased resistance to corn rootworms, particularly a corn plant transformed with a modified CryIIIA protein yielding increased toxicity towards corn rootworms, particularly *Diabrotica virgifera virgifera*.

Other objects and advantages of this invention will become evident from the following description.

DETAILED DESCRIPTION OF THE INVENTION

In this invention, certain amino acid residues important for toxicity of CryIII proteins are identified. In accordance with this invention, the CryIIIA protein was found to have some toxicity to the corn rootworm *Diabrotica virgifera virgifera*. Some of the designed CryIIIA protein mutants, wherein single amino acid residues were replaced by alanine, showed a significantly decreased toxicity towards this corn rootworm. In accordance with this invention, the substitution of these amino acids by other amino acids improves the toxicity of the CryIIIA protein. Alternatively, receptor binding assays are conducted to analyze the binding of the mutant Bt proteins to their gut receptor, since in general there is a correlation between binding characteristics and toxicity. Toxicity can be measured by assaying mortality (number of insects killed) and/or feeding inhibition (amount of food ingested) (see *Methods for the study of Pest Diabrotica*, 1986, eds. Krysan J. L. and Miller, T. A., Springer-Verlag, New York) Receptor binding can be analyzed by following well known procedures, such as those described by Van Rie et al. (1990, supra) and Slaney et al. (1992, supra).

"Corn rootworms", as used herein, refer to insects of the genus Diabrotica, including the banded cucumber beetle, the northern corn rootworm, the western spotted cucumber beetle, the southern corn rootworm, the western corn rootworm and the Mexican corn rootworm (see Krysan, 1986, in "Methods for the study of Pest Diabrotica", pp. 1–23, eds. Krysan J. L. and Miller, T. A., Springer-Verlag, New York), either in larval or adult stage. The modified proteins of this invention having improved corn rootworm toxicity, are preferably used to protect fields of corn plants by contacting the corn rootworms with the modified protein. Although corn is a very important crop infested by corn rootworms, many other host plants are known. A modified toxin according to this invention, having high toxicity to corn rootworms, can protect any plant attacked by corn rootworms, such as cucurbits, sweet potatoes, and legumes, including peanuts, common bean, and cowpea (Krysan, 1986, supra).

"A CryIII protein", as used herein, refers to a Bt ICP toxin to at least one Coleopteran insect, e.g. the CryIIIA protein (EP 0149162, EP 0318143), the BtPGSI208 protein (EP 0458819), the BtPGSI245 protein (EP 0458819), the CryII-ICb protein (PCT patent publication WO 92/13954), the BtI109P or CryIIID protein (PCT patent publication WO 91/16433), and the BtI260 protein (PCT patent publication WO 91/16433), as well as insecticidally effective parts and functionally equivalent variants thereof. Other Bt proteins have been described to be active to Coleopteran insects (Koziel et al., 1993, supra), including proteins such as the CryIX or 81k protein (PCT patent publication WO 90/13651), the PS50C protein (EP 0498537) and the PS86A1 protein (EP 0500311). "Functionally equivalent variants", also referred to herein as "variants", of a certain protein are proteins that differ in some amino acids, or have some amino acids added (e.g. a fusion protein, see Vaeck et al., 1987, Nature 327, 33–37) or deleted (e.g. N- or C-terminal truncation), as long as the proteins have substantially the same insecticidal activity. Indeed, several variants of a Bt protein in which some amino acids are changed into others without significantly changing activity and/or specificity can be found in nature (Höfte & Whiteley, 1989, supra) or can be made by recombinant DNA techniques. Such variants include proteins comprising at least the toxin part of the CryIII protein. "CryIII toxin part", as used herein, refers to a form of lower molecular weight, derivable from a CryIII protein, and retaining substantially the same toxicity as the CryIII protein. A preferred CryIII toxin is that obtained by protease, e.g. trypsin, cleavage. Variants of a CryIII protein, as used herein, also include proteins containing the specificity- and toxicity-determining region of the CryIII protein, e.g. in a hybrid with another protein, such as another Bt ICP, provided the CryIII toxicity is substantially retained therein. A CryIII protein, as used herein, includes any protein containing domain II of a CryIII protein, preferably domain II of the CryIIIA protein. A CryIII protein can also have an activity against other inset pests, e.g. against Lepidoptera (PCT patent publication WO 93/04587).

Following the teachings of this invention, CryIII proteins can be modified to have an altered, preferably increased, toxicity for a certain target insect. "Modified CryIII protein", in accordance with this invention, refers to a CryIII protein having at least one amino acid difference with the native CryIII protein, so that the toxicity of this protein towards the target insect is altered, preferably increased, by this amino acid modification. A modified CryIII protein, differing in one amino acid from the native protein and being significantly less toxic towards the target insect, allows the direct identification of this amino acid position as involved in toxicity (provided no gross structural changes are introduced), and thus has considerable value in improving toxicity. In accordance with this invention, the identification of these amino acid positions involved in toxicity allows the construction of modified proteins having increased toxicity to the target insect. Preferred embodiments of modified CryIII proteins in accordance with this invention are the modified CryIIIA proteins having altered toxicity to *Diabrotica virgifera virgifera*, as shown in Table 1. Modified CryIII proteins also include hybrid proteins made by transferring a functional part of a modified CryIII protein to another Bt ICP protein, such as a CryI toxin.

The term "functional part of a modified CryIII protein", as used herein, refers to a part or domain of a modified CryIII protein with a specific function, including parts at different locations in the primary protein sequence, that together form a functional unit of the protein, that can be transferred or added to another protein, such as another Bt ICP, for providing a new hybrid protein with at least one functional characteristic (e.g., the binding, specificity and/or toxicity characteristics) of the modified CryIII toxin (Ge et al., 1991, supra), that is different from that of the native CryIII protein. Such a hybrid protein can have an enlarged host range and/or an improved toxicity. For example, domain II, preferably the regions protruding from sheets 1 and 2 in domain II of a modified CryIIIA protein of this invention, yielding improved toxicity to corn rootworms, can replace the native domain II in another protein, such as another Bt ICP.

A "cryIII gene", such as the "cryIIIA gene", as used herein, is a DNA sequence encoding a CryIII protein, such as a CryIIIA protein, and including necessary regulatory sequences so that a CryIII protein, such as a CryIIIA protein, can be expressed. A cryIII gene does not necessarily need to be expressed everywhere at all times, expression can be periodic (e.g. at certain stages of development in a plant) and/or can be spatially restricted (e.g. in certain cells or tissues in a plant), mainly depending on the activity of regulatory elements provided in the chimeric gene or in the site of insertion in the plant genome.

The "modified cryIII gene", such as the "modified cryIIIA gene", as used herein, is a gene comprising a DNA sequence (the "modified coding region") encoding a modified CryIII protein, such as a modified CryIIIA protein. An example of a modified cryIII coding region is the modified cryIIIA coding region of SEQ ID no 3, having each 'nnn' triplet replaced by an alanine codon, preferably GCC, and any DNA sequence with substantial sequence homology thereto. "Substantial sequence homology" to a DNA sequence, as used herein, refers to DNA sequences differing in some, most or all of their codons from another DNA sequence but encoding the same or substantially the same protein. Indeed, because of the degeneracy of the genetic code, the codon usage of a particular DNA coding region can be substantially modified, e.g. so as to more closely resemble the codon usage of the genes in the host cell, without changing the encoded protein. Changing the codon usage of a DNA coding region to that of the host cell has been described to be desired for gene expression in foreign hosts (e.g. Bennetzen & Hall, 1982, J. Biol. Chem. 257, 3026–3031.; Itakura, 1977, Science 198, 1056–1063). Codon usage tables are available in the literature (Wada et al., 1990, Nucl. Acids Res. 18, 2367–1411; Murray et al., 1989, Nucl. Acids Res. 17(2), 477–498) and in the major DNA sequence databanks (e.g. at EMBL in Heidelberg, Germany). Accordingly, recombinant or synthetic DNA sequences can be constructed so that the same or substantially the same proteins with substantially the same insecticidal activity are produced (Koziel et al., 1993, Bio/technology 11, 194–200; Perlak et al., 1993, Plant Mol. Biol. 22, 313–321). "Homology", as used herein, in the context of DNA or protein sequence comparisons, refers to structural or sequence similarity without the need for any functional similarity, nor any evolutionary relationship. A modified cryIII gene or modified cryIIIA gene has all appropriate control regions so that the modified CryIII protein can be expressed in a host cell, e.g. for expression in plants, a plant-expressible promoter and a 3' termination and polyadenylation region active in plants.

A "chimeric modified cryIII gene", as used herein, refers to a modified CryIII gene wherein the modified cryIII coding region is inserted in between controlling elements of different origin, e.g. a DNA sequence encoding the modified CryIII protein under the control of a plant-expressible promoter, and fused to 3' termination and polyadenylation sequences active in plant cells. A "modified cryIII coding region", such as a "modified cryIIIA coding region" as used herein, is that part of the modified cryIII gene, such as a cryIIIA gene, that is translated in a modified CryIII protein, such as a CryIIIA protein, i.e. the nucleotide sequence from the start codon to the stop codon.

The "CryIIIA protein" according to this invention refers to the protein of SEQ ID No. 2 or any functionally equivalent variant thereof, such as the protein described in Herrnstadt et al. (1987, Gene 57, 37 46), or a protein containing a functional part of the CryIIIA protein, such as a protein containing domain II of the CryIIIA protein. A CryIIIA protein as used in this invention includes the approximately 72 kd CryIIIA protein encoded by the cryIIIA coding sequence of SEQ ID No. 1, the lower molecular weight CryIIIA toxin, as well as proteins of intermediate molecular weight. The term "toxin", such as a "CryIIIA toxin", as used herein, refers to a shortened, truncated form of a Bt ICP, such as a shortened, truncated from a CryIIIA protein, e.g. as obtained by protease treatment, whereby this truncation does not substantially alter the toxicity of the protein. A CryIIIA toxin of 66 kD has been reported to retain toxicity. This protein has 57 N-terminal amino acids removed by proteases (McPherson et al., 1988, Bio/Technology 6, 61; Höfte et al., 1987, Nucl. Acids Res. 15, 7183). Also, N-terminal deletions of 47 and 49 amino acids, as well as the replacement of the second amino acid (asparagine) by aspartic acid, and the replacement of the 49 N-terminal amino acids by a methionine-aspartic acid dipeptide were found not to affect toxic activity of the CryIIIA protein. These truncated variants of the CryIIIA protein with substantially the same toxicity are included in the term "CryIIIA protein" as used herein. At the C-terminal part of the CryIIIA protein, any major deletion was found to result in a non-toxic protein (McPherson et al., 1988, supra).

A "modified CryIIIA protein" of this invention refers to a CryIIIA-derived protein of this invention with altered, preferably increased, Coleopteran, preferably corn rootworm, insecticidal activity. An example of a modified CryIIIA protein in accordance with this invention is the CryIIIA protein having the proline amino acid at position 348 of SEQ ID no 2 replaced by alanine, this change yielding a several-fold increase of toxicity towards the Colorado potato beetle. An example of a modified CryIIIA protein having altered toxicity to corn rootworms is the CryIIIA protein differing in at least one of the amino acid residues Phe346, Gln347, Pro348, Gly349, Tyr350, Trp411, Pro412, Tyr416 or Lys442 of SEQ ID no 2, preferably Gly349, Tyr350, Trp411, Pro412, or Tyr416 of SEQ ID no 2 from the native CryIIIA protein, e.g. by alanine replacement, so that the activity towards corn rootworms, particularly Diabrotica virgifera virgifera, is altered. Protection of a corn plant against corn rootworms is preferably accomplished by contacting the corn rootworm with a modified CryIIIA protein yielding increased toxicity, preferably by expressing the chimeric modified cryIIIA gene encoding such a modified CryIIIA protein in the cells of a corn plant. A modified CryIIIA protein includes modifications to the full length CryIIIA protein of about 72 kD, to the toxin of about 66 kD, and any proteins of intermediate molecular weight, as well as functionally equivalent variants, characterized in that this modification alters, preferably increases, toxicity towards corn rootworms, preferably Diabrotica virgifera virgifera, when compared to the CryIIIA protein. A modified CryIIIA protein of this invention preferably has only a small number, particularly less than 30, more particularly less than 20, preferably less than 10 amino acids changed as compared to the CryIIIA protein, preferably as compared to the CryIIIA protein of SEQ ID No. 2. A substantial increase in toxicity can already be obtained by replacing only 1 amino acid, as has been shown for the Colorado potato beetle CryIIIA alanine-mutant at position 348, but it is preferred that more than one amino acid is changed to improve toxicity. A modified CryIIIA protein, differing from the native CryIIIA protein in one amino acid, and resulting in a significantly lower toxicity to the target inset when compared to the native protein, allows the direct identification of this amino acid as involved in toxicity. In accordance with this invention, this amino acid can be replaced by a more preferred amino acid to obtain a modified protein with improved toxicity.

Proper application of a modified CryIII protein of this invention, yielding improved coleopteran toxicity, preferably corn rootworm toxicity, to plants, preferably, corn plants, protects these plants against these pest insects. Since corn rootworm larvae feed on corn root tissue and corn rootworm adults feed on corn leaves and silks, protection of corn is most conveniently achieved by expressing a chimeric gene encoding a modified CryIII protein yielding improved toxicity, preferably a modified CryIIIA protein yielding improved toxicity, in a corn plant, preferably at least in the roots of a corn plant. Such a transgenic plant contains the chimeric modified cryIII gene as a stable genomic insert. This way, a very cost-effective and reliable control of corn rootworms, particularly Diabrotica virgifera virgifera, is obtained.

The following steps are followed to construct the new mutant CryIII proteins: locate the amino acids responsible for receptor binding/toxicity in the region(s) identified to be involved in this receptor binding/specificity; change these identified amino acid positions, or the amino acids at these positions and those amino acids immediately adjacent to these positions, randomly into other amino acids; and combine all or some of the mutant amino acids, identified as increasing toxicity of the protein ("up mutants"), in a single mutant protein that has a significantly higher toxicity.

It is believed that specific regions of domain II of the Cry proteins are responsible for receptor-binding. Consequently, this domain was chosen as the region to identify amino acids, preferably solvent-accessible amino acids, in the three-dimensional structure of the CryIII protein involved in toxicity. A more detailed description of the above general steps is given below:

1) The identification of amino acids to be substituted in order to alter the toxicity is done by site-directed mutagenesis. A particular type of site-directed mutagenesis, specifically suited for such analysis, is named alanine-scanning mutagenesis (Cunningham & Wells, 1989, Science 244, 1081–85). In this mutational method, each amino acid position to be tested is sequentially changed to alanine. An alanine-mutant is hence constructed for each position of interest. Alanine replacement eliminates all side chain information beyond the beta carbon, without introducing extreme electrostatic or steric effects. In this way, the chances for structural distortion of the mutant protein, at positions other than the mutated position, are minimized. Only solvent accessible amino acids are expected to be able to directly contribute to receptor binding. Therefore, the identification of amino acids involved in toxicity primarily focused on those amino acids that have a high solvent-accessibility, and those amino acids that are located adjacent to these amino acids in the three-dimensional structure of the protein.

On the basis of the three dimensional model of the CryIIIA protein (Li et al., 1991, supra), the relative accessibility of the amino acid side chains of this protein were calculated. All modelling was done using the Brugel package (Delhaise et al., 1984, J. Mol. Graph. 2, 103–106). Starting from the X-ray crystallographic C-alpha coordinates as obtained from Li et al. (1991, supra) the main chain was modeled using the Brugel spare parts approach (Claessens et al., 1989, Protein Eng. 2, 335–345). In a second step, all side chains according to the modeled protein were modified and a full hydrogen model was generated. The side chain orientation was determined using the "Death and elimination theorem" (Desmet et al., 1992, Nature 356, 539–542). The obtained structure was energy-minimized by 250 steps of steepest descent and 500 steps of conjugated gradient. The relative solvent accessibilities of the side chains were determined according to the Brugel package (Delhaise et al., 1984, supra). The values obtained for the side chains of amino acid positions 291 to 506, comprising domain II, are shown in Table 3.

The inventors have found that amino acids having side chains with a relative solvent accessibility of 40% or more are a primary choice for substitution to alanine. Amino acids, having side chains with relative solvent accessibilities between 30 to 40% are also replaced by alanine. Amino acids whose side chains have less than 40% relative solvent accessibility but which are, in the primary sequence, located at a maximum distance of 3 amino acid positions from, an amino acid having a relative solvent accessibility of at least 40%, are also replaced by alanine.

For proteins for which no three-dimensional structure is known or available, there are several other possibilities. One is to construct a three dimensional model by homology modelling (also known as comparative model building) and then calculate the relative accessibility of the side chains from the newly developed model. Another possibility is to assume, in a first approximation, that the relative accessibility of the side chains at the aligned positions will correlate with the accessibility of the corresponding amino acids of CryIIIA. Alanine mutants can be constructed by a variety of mutagenesis methods, amongst others the PCR overlap extension method (Ho et al., 1989, Gene 77, 51–59). Homology modelling and amino acid alignment based on the known three-dimensional structure of the CryIIIA protein have been used for structure determination of other Cry proteins, such as CryI proteins (Lu et al., 1993, supra; Smith & Ellar, 1992, supra).

The alanine-mutants are then tested in receptor binding assays and/or toxicity assays, preferably toxicity assays. Substitution of an amino acid, that is part of the receptor binding epitope, to alanine is expected to yield a mutant protein with altered—usually decreased—binding affinity. Such a mutant ICP is also expected to have an altered—usually decreased—toxicity. Mutants with altered toxicity or binding affinity are subjected to further analysis. The altered toxicity or binding affinity of these mutants can be due to two different phenomena. It can be due to the intrinsic effect of the mutation on receptor binding. In that case a lower toxicity of the mutant must be interpreted so as to assign involvement in receptor binding to this position. Lower toxicity may also be due to misfolding or structural distortion propagated beyond the mutated site. The structural stability of mutant ICPs can be analyzed by a variety of methods including toxicity to another target insect, crystal formation, solubilization, monoclonal antibody binding analysis, protease resistance, fluorometric monitoring of unfolding and circular dichroism spectrum analysis. In the case of structural distortion, it is impossible to determine the functional role of this position by alanine replacement. However, a more conservative amino acid substitution may yield a correctly folded mutant protein which allows to determine the functional role of this position.

2) The amino acid positions, identified in step 1, as well as those immediately adjacent to these positions in the three-dimensional structure, preferably those amino acids whose C-alpha atom is at a maximum distance of about 7 Ångstrom from the C-alpha atom of the amino acid identified in step 1, are randomized. This means that a set of 20 different mutants, representing each type of amino acid, is generated for each position of interest (the original amino acid and the alanine substitution function as a control). This method is further referred to as "amino acid randomization". Such mutants may be generated by a variety of methods, e.g. following the PCR overlap extension method (Ho et al., 1989, supra). These mutant proteins are then tested in toxicity assays on the target insect. Mutants at each position that are more toxic, e.g. yielding higher mortality or increased feeding inhibition than the wild type protein, are selected. Such mutants with improved toxicity are termed "up-mutants". Alternatively, it is also possible to select potential up-mutants on the basis of increased binding affinity using receptor binding assays, as described above. Those mutants with increased binding affinity can then be tested in toxicity assays to select the up mutant proteins.

3) All or some of the "up mutant" amino acids, identified in step 2, are combined in a single modified protein. According to additivity principles, mutations in non-interacting parts of a protein should combine to give simple additive changes in the free energy of binding (Lowman and Wells, 1993, J. Mol. Biol, 234, 564–578). Increases in toxicity are thus accumulated by combining several single mutants into one multiple mutant. Finally a modified protein with improved toxicity is designed, which comprises some or all, preferably all, of the up-mutant amino acids previously identified.

Optionally, to locate the region involved in receptor binding/specificity, either hybrid crystal proteins are constructed by exchanging structural domains between the crystal proteins (a); or homolog scanning mutagenesis is performed: exchange homologous secondary structural elements between two crystal proteins (b).

To apply strategy a or b, the availability of two proteins with a different level of toxic activity on the target insect is required. Preferably, the toxicity of these two proteins differs by a factor of at least 10. In the current application, both approaches start with an alignment with the CryIIIA sequence (see Li et al., 1991, supra) of the proteins involved. Upon alignment of different ICP amino acid sequences, five conserved blocks can be identified (Höfte and Whiteley, 1989, supra). Most of these blocks are located in domain interfaces in the CryIIIA three dimensional structure (Li et al., 1991, supra). The transition from domain I to domain II is located in conserved block II, whereas the transition from domain II to domain III is located in conserved block III. Consequently, the identification of the borders of the three structural domains in ICPs is relatively straightforward. The localization of these borders is required to apply strategy a). Once the location of the three structural domains has been determined in both proteins, gene fragments corresponding to those structural domains are exchanged between the two proteins. If useful restriction enzyme sites happen to be located just at the border between structural domains, the corresponding restriction enzymes can be used to obtain gene fragments corresponding to the structural domains. If no such sites are present, they may be generated through silent mutations. Such silent mutations may not always be possible however. Therefore, it may be preferred to exchange gene fragments corresponding to structural domains by splice overlap extension using PCR (Horton et al., 1989, Gene 77, 61–68). Following construction, hybrid or mutant genes are then expressed in *E. coli* or crystal minus *B. thuringiensis* strains. The mutant or hybrid proteins are then tested in toxicity assays on the target insect. By comparing the toxicity of the parental and hybrid proteins and considering the sequences of the hybrid proteins, the region(s) which are responsible for the higher activity of one of the ICPs are located. Since in general there is a correlation between binding and toxicity, this region is likely to correspond to or include the receptor binding region of the ICP with the highest activity on the target insect. This can be checked in receptor binding assays.

Knowledge of the location of the various secondary structural elements in the proteins of interest is desirable to apply strategy b). Indeed, the exchange of gene fragments corresponding to such elements is likely to increase the chances of obtaining structurally stable hybrid proteins. Gene fragments can, however, be exchanged between ICP genes without knowledge of the location of secondary structural elements.

The same three options (using available restriction sites, creating restriction sites through silent mutations, or using PCR splicing) apply to homolog scanning mutagenesis.

In accordance with this invention, amino acids of domain II of a *Bt* ICP, with side chains having a relative solvent-accessibility of at least 40% and adjacent amino acids, maximally 3 positions away from this amino acid in the primary sequence of the protein, preferably these amino acids with side chains having a relative solvent-accessibility of at least 30%, more preferably amino acids with side chains having a relative solvent-accessibility of at least 40%, are the prime targets to identify amino acids involved in toxicity, such as by alanine-scanning mutagenesis. Some mutant amino acids may cause gross structural changes to the protein, as detected by altered or lack of crystal formation, solubility, protease resistance, monoclonal antibody binding, and the like. The role of these amino acid positions in toxicity can be tested by making a more conservative amino acid substitution. Particularly preferred regions for amino acid replacement are the protruding regions of domain II or a *Bt* ICP. By "protruding regions of domain II", as used herein, are meant the loops and beta-strands projecting out of domain II into the solvent and folded towards the apex of the molecule (i.e. away from the interface of domain II with domain III) or located at the apex of the molecule (e.g. for the CryIIIA molecule, the apex is the small region at the bottom part in the three-dimensional ribbon presentation of FIG. 4a in Li et al., 1991, supra). Even more preferred regions are the loops and beta-strands protruding from sheets 1 and 2 of domain II and located at the apex of the molecule, even more particularly the solvent exposed parts thereof. The protruding regions of sheets 1 and 2 of domain II in the CryIIIA protein consist of (positions refer to SEQ ID no 2): for sheet 1: 1) the region delineated by amino acid positions 345 and amino acid positions 358, and 2) the region delineated by amino acid position 380 and amino acid position 390; and for sheet 2: 1) the region delineated by amino acid position 406 and amino acid position 418, and 2) the region delineated by amino acid positions 440 and 448.

Particularly preferred amino acids for amino acids randomization are amino acids located at structurally analogous positions to amino acids located in the protruding regions of domain II of the CryIIIA protein. These protruding regions in domain II of the CryIIIA protein are formed by: —the part of beta-strand 2 departing from sheet 1, beta-strand 3r and their connecting loop in sheet 1; —the part of beta-strand 6 departing from sheet 2, beta-strand 7r and their connecting loop in sheet 2; —the loop connecting alpha helix 8 and beta-strand 2 in sheet 3; —the loop connecting beta-strands 10 and 11 in sheet 3; —the loop connecting beta strands 8 and 9 in sheet 2; and —the loop connecting beta-strands 4 and 5 in sheet 1, as shown in FIG. 2a and FIG. 4a in Li et al. (1991, supra) which is incorporated herein by reference. By "structurally analogous positions" in different *Bt* proteins, as used herein, are meant amino acid positions that are located in a similar structural element in the three dimensional structure or model of these *Bt* proteins. Included in these structurally analogous positions are amino acids of a BL ICP, preferably a CryIII protein, at positions analogous to amino acid positions Phe346, Gln347, Pro348, Gly349, Tyr350, Trp411, Pro412, Tyr416 or Lys442 in the CryIIIA protein of SEQ ID No. 2, preferably amino acids at positions structurally analogous to amino acids Gly349, Tyr350, Trp411, Pro412, or Tyr416 of the CryIIIA protein of SEQ ID no 2. Indeed, it is believed that the three-dimensional structure of all Cry protein toxins, including CryI protein toxins, largely resembles the CryIIIA structure described in Li et al. (1991, supra). In accordance with this invention, regions of another *Bt* protein at a similar location as the identified protruding regions in the CryIIIA protein, and amino acids located at positions structurally analogous to the amino acids positions identified for CryIIIA and described herein above are targets for alanine scanning mutagenesis and/or random amino acid replacement, thus yielding modified proteins with improved toxicity to the target insect.

In accordance with this invention, analysis of the X-ray crystallographic structure, or computer-predicted structure analysis and amino acid alignment (based on the known CryIIIA structure) of a Cry protein, identifies regions or amino acids located at structurally analogous positions to the identified positions of the CryIIIA protein. Indeed, when analyzing a three-dimensional model of a Cry protein, different from CryIIIA, such as a CryI protein, it is believed that certain regions of domain II will also be protruding from the molecule and will also be directed to, or located at, the molecular apex of the protein molecule. Some of these regions are believed to be responsible for specific binding to the target receptor. In accordance with this invention, such identified regions are the prime targets for modification of amino acid residues to improve toxicity.

This invention is particularly suited for improving the toxicity of a *Bt* protein that has a rather weak toxicity to a target insect. Indeed, the toxicity of this Cry protein can be increased by combining amino acid mutations in the protein, each yielding an increased toxicity when compared to the amino acid present in the native protein.

An insecticidally effective part of the modified cryIII gene of this invention, such as an insecticidally effective part of a modified cryIIIA gene, encoding an insecticidally effective portion of its protein, can be made in a conventional manner. An "insecticidally effective part" of the modified cryIII gene refers to a gene comprising a DNA coding region encoding a polypeptide that has fewer amino acids than the full length modified CryIII protein but that still retains toxicity to Coleoptera, e.g. a gene encoding the N-terminally truncated modified CryIIIA toxin, such as the about 66 kD modified CryIIIA toxin.

In order to express all or an insecticidally effective part of the modified cryIII gene in *E. coli*, in other *Bt* strains and in plants, suitable restriction sites can be introduced, flanking each gene or gene part. This can be done by site-directed mutagenesis, using well-known procedures (Slanssens et al., 1989, Nucl. Acids Res. 12, 4441–4454; White et al., 1989, Trends in Genet. 5, 185–189).

In order to improve expression in foreign host cells such as plant cells, it may be preferred to alter the modified cryIII coding region or its insecticidally effective part to form an equivalent, artificial modified cryIII coding region. Expression is improved by selectively inactivating certain cryptic regulatory or processing elements present in the native sequence as described in PCT publications WO 91/16432 and WO 93/09218. This can be done by site-directed mutagenesis or site-directed intron-insertion (WO 93/09218), or by introducing overall changes to the codon usage, e.g., adapting the codon usage to that most preferred by the host organism (EP 0385962, EP 0359472, PCT publication WO 93/07278, Murray et al., 1989, supra) without significantly changing, preferably without changing, the encoded amino acid sequence. Small modifications to a DNA sequence such as described above can be routinely made by PCR-mediated mutagenesis (Ho et al., 1989, supra; White et al., 1989, supra). For major changes to the DNA sequence, DNA synthesis methods for available in the art (e.g. Davies et al., 1991, Society for Applied Bacteriology, Technical Series 28, pp. 351–359).

For obtaining enhanced expression in monocot plants such as corn, a monocot intron can be added to the chimeric modified cryIII gene (Callie et al., 1987, Genes & Development 1, 1183–1200; PCT publication WO 93/07278).

The chimeric modified cryIII gene and its insecticidally effective gene part, preferably the chimeric modified cryIIIA gene of this invention, encoding an insecticidally effective portion of the modified CryIIIA protein, can be stably inserted in a conventional manner into the nuclear genome of a single plant cell, and the so-transformed plant cell can be used in a conventional manner to produce a transformed plant that is insect-resistant. Corn cells can be stably transformed (e.g. by electroporation) using wounded or enzyme-degraded intact tissues capable of forming compact embryogenic callus (such as corn immature embryos), or the embryogenic callus (such as type T callus in corn) obtained thereof, as described in PCT patent publication WO 92/09696. Other methods for transformation of corn include the methods using particle-mediated transformation as described by Fromm et al. (1990, Bio/Technology 8, 833–839) and Gordon-Kamm et al. (1990, The Plant Cell 2, 603–618) and in EPO 270356.

Alternatively, a disarmed Ti plasmid, containing the insecticidally effective chimeric modified cryIII gene, in *Agrobacterium tumefaciens* can be used to transform the plant cell, and thereafter, a transformed plant can be regenerated from the transformed plant cell using the procedures described, for example, in EP 0116718, EP 0270822, PCT publication WO 84/02913 and EP 0242246 (which are also incorporated herein by reference), and in Gould et al. (1991, Plant Physiol. 95, 426–434), particularly the method described in PCT publication WO 94/00977. Preferred Ti-plasmid vectors each contain the insecticidally effective chimeric modified cryIII gene between the border sequences, or at least located to the left of the right border sequence, of the T-DNA of the Ti-plasmid. Of course, other types of vectors can be used to transform the plant cell, using procedures such as direct gene transfer (as described, for example in EP 0223247), pollen mediated transformation (as described, for example in EP 0270356, PCT publication WO 85/01856, and U.S. Pat. No. 4,684,611), plant RNA virus-mediated transformation (as described, for example in EP 0067553 and U.S. Pat. No. 4,407,956), and liposome-mediated transformation (as described, for example in U.S. Pat. No. 4,536,475).

A resulting transformed plant, such as a transformed corn plant, can be used in a conventional plant breeding scheme to produce more transformed plants with the same characteristics or to introduce the modified cryIII gene, such as a modified cryIIIA gene, or an insecticidally effective part thereof in other varieties of the same or related plant species. Seeds, which are obtained from the transformed plants, contain the chimeric modified cryIII gene or its insecticidally effective part as a stable genomic insert. Cells of the transformed plant can be cultured in a conventional manner to produce the CryIII protein or insecticidally effective portions thereof, which can be recovered for use in conventional insecticide compositions against Coleoptera, particularly corn rootworms (U.S. patent application Ser. No. 821,582; EP 0193259).

The modified cryIII coding region or its insecticidally effective part is inserted in a plant cell genome so that the inserted coding region is downstream (i.e., 3') of, and under the control of, a promoter which can direct the expression of the gene part in the plant cell. This is preferably accomplished by inserting the chimeric modified cryIII gene or its insecticidally effective part in the plant cell genome. Preferred promoters include: the strong constitutive 35S promoters (the "35S promoters") of the cauliflower mosaic virus of isolates CM 1841 (Gardner et al., 1981, Nucleic Acids Research 9, 2871–2887), CabbB-S (Franck et al., 1980, Cell 21, 285–294) and CabbB-JI (Hull and Howell, 1987, Virology 86, 482–493); the ubiquitin promoter (EP 0342926), and the TR1' promoter and the TR2' promoter which drive the expression of the 1' and 2' genes, respectively, of the T-DNA (Velten et al., 1984, EMBO J. 3, 2723–2730). Alternatively, a promoter can be utilized which is not constitutive but rather is specific for one or more tissues or organs of the plant, preferably root tissue, whereby the inserted chimeric modified cryIII gene or its insecticidally effective part is expressed only in cells of the specific tissue(s) or organ(s). For example, the chimeric modified cryIIIA gene or its insecticidally effective gene part could be selectively expressed in the roots of a corn plant by placing the insecticidally effective gene part under the control of a promoter such as the metallothionin promoter of EP 0 452 269, or the promoters described by Conkling et al. (1990, Plant Physiol. 93, 1203) and Opperman et al. (1994, Science 263, 221). Another alternative is to use a promoter whose expression is inducible (e.g., by insect feeding or by chemical factors). Known wound-induced promoters inducing systemic expression of their gene product throughout the plant are also of particular interest.

The modified cryIII coding region, or its insecticidally effective part, is inserted in the plant genome so that the inserted coding region is upstream (i.e., 5') or suitable 3' end transcription regulation signals (i.e., transcript termination and polyadenylation signals). This is preferably accomplished by inserting the chimeric modified cryIII gene in the plant cell genome. Preferred polyadenylation and transcript formation signals include those of the 35S gene (Mogen et al., 1990, The Plant Cell 2, 1261–1272), the octopine synthase gene (GloIen et al., 1984, EMBO J 3, 835–845) and the T-DNA gene 7 (Velten and Schell, 1985, Nucl. Acids Res. 13, 6981–6998), which act as 3'-untranslated DNA sequences in transformed plant cells.

The chimeric modified cryIII gene, or its insecticidally effective gene part, can optionally be inserted in the plant genome as a hybrid gene (EP 0 193 259; Vaeck et al., 1987, supra) under the control of the same promoter as the coding region of a selectable marker gene, such as the coding region of the neo gene (EP 0.242.236) encoding kanamycin resistance, so that the plant expresses a fusion protein.

All or part of the modified cryIII coding region can also be used to transform bacteria, such as a B. thuringiensis which has insecticidal activity against Lepidoptera, or a B. thuringiensis which produces other insecticidal corn rootworm toxins with a different mode of action (Lereclus et al., 1992, Bio/Technology 10, 418–421; Gelernter & Schwab, 1993, In Bacillus thuringiensis, An Environmental Biopesticide; theory and Practice, pp. 89–104, eds. Entwistle, P. F., Cory, J. S., Bailey, M. J. and Higgs, S., John Wiley & Sons Ltd.). Thereby, a transformed Bt strain is produced which is useful for combatting a wide spectrum of lepidopteran and coleopteran insect pests or for combatting corn rootworms in such a manner that resistance is prevented or delayed (EP 0108403). Preferred promoter and 3' termination and polyadenylation sequences for the chimeric modified cryIII gene are derived from Bacillus thuringiensis genes, such as the native ICP genes.

Alternatively, the modified coding region of the invention can be inserted and expressed in endophytic and/or root-colonizing bacteria, such as bacteria of the genus Pseudomonas or Clavibacter—e.g. under the control of a Bt ICP gene promoter and 3' termination and polyadenylation sequences. Successful transfer and expression of ICP genes into such bacteria has been described by Stock et al. (1990, Can. J. Microbiol. 36, 879–884), Dimock et al. (1989, In Biotechnology, Biopesticides and Novel Plant Pest Resistance Management, eds. Roberts, D. W. & Granados, R. R., pp.88–92, Boyce Thompson Institute for Plant Research, Ithaca, N.Y.), and Waalwijk et al. (1991, FEMS Microbiol. Lett. 77, 257–264). Transformation of bacteria with all or part of the modified cryIII coding region of the invention, incorporated in a suitable cloning vehicle, can be carried out in a conventional manner, preferably using conventional electroporation techniques as described in Mahillon et al. (1989, FEMS Microbiol. Letters 60, 205–210), in PCT patent publication WO 90/06999, Chassy et al. (1988, Trends Biotechnol. 6, 303–309) or other methods, e.g., as described by Lereclus et al. (1992, Bio/Technology 10, 418).

The modified CryIII-producing strain can also be transformed with all or an insecticidally effective part of one or more foreign Bt genes such as: the bt2 gene (EP 0193259) or the bt2618 gene (PCT publication 94/05771) or another Bt gene coding for an anti-Lepidoptera protein; and the bt109P gene (PCT publication WO 91/16433) or the cryIIIB or cryIIIB2 gene (Donovan et al., 1992, Appl. Environm. Microbiol. 58, 3921–37), or another gene encoding an anti-Coleoptera protein. Thereby, a transformed Bt strain can be produced which is useful for combatting an even greater variety of insect pests (e.g., Lepidoptera and/or additional Coleoptera) or for preventing or delaying the development of insect resistance (EP 0408403).

For the purpose of combatting insects by contacting them with the modified CryIII protein, e.g. in the form of transformed plants or insecticidal formulations, any of the above described variants of the modified CryIII protein, with substantially the same insecticidal activity, as well as any DNA sequence encoding such variants of the modified CryIII protein, can be used.

The following Examples are offered by way of illustration and not by way of limitation. The sequence listing referred to in the Examples is as follows:

Sequence Listing

SEQ ID no 1: The native cryIIIA coding region and the encoded CryIIIA protein.

SEQ ID no 2: The amino acid sequence of the native CryIIIA protein.

SEQ ID no 3: The nucleotide sequence of an artificial modified cryIIIA coding region, with each 'nnn' encoding an amino acid involved in corn rootworm toxicity. This DNA sequence has been optimized for expression in corn as described in the Examples.

SEQ ID no 4: A modified CryIIIA protein with 'Xaa' representing an amino acid residue involved in corn rootworm toxicity.

Unless otherwise stated in the Examples, all procedures for making and manipulating recombinant DNA are carried out by the standardized procedures as described in volume 1 and 2 of Ausubel et al., Current Protocols in Molecular Biology, Current Protocols, USA (1994) and Sambrook et al., Molecular Cloning - A Laboratory Manual, Second Ed., Cold Spring Harbor Laboratory Press, N.Y. (1989).

EXAMPLES

1. Alanine-scanning Mutagenesis

Domain II of the CryIIIA protein of SEQ ID no 2 was chosen as region to analyze individual amino acids involved in toxicity. Replacement of amino acids with high solvent-accessibility and their neighboring amino acids by alanine, as described in the detailed description, identified amino acid positions of domain II involved in toxicity. Mutant cryIIIA coding regions, derived from the cryIIIA coding region of SEQ ID no 1, were constructed using the PCR overlap extension method (Ho et al., 1989, supra). For each mutant gene, four primers were used: two 'outer', 'wild type' primers and two 'inner', 'mutagenic' primers. These mutagenic primers were complementary to a certain region of the cryIIIA coding region of SEQ ID no 1, except at one particular codon, which was changed into an alanine codon. GCA was chosen as the alanine codon, since it is the most frequently used alanine codon in the cryIIIA coding sequence of SEQ ID no 1. The two mutagenic primers partially overlap. Two PCR reactions were performed, each reaction using a primer pair containing an outer wild type primer and a mutagenic primer. The amplified products from these 'primary' PCR reactions were gel-purified, combined and used as template in a 'secondary' PCR reaction containing only the outer primers. The resulting amplification product was purified directly from the PCR reaction mixture and digested with two restriction enzymes. The digested PCR fragments were purified and ligated into the appropriate vector, digested with the same two restriction enzymes sites. For some mutants, pBT3λ2 digested with appropriated restriction enzymes was used as vector fragment. This plasmid was constructed by cloning the HindIII fragment containing the cryIIIA gene into the HindIII site of pUC19. In this case, the complete—mutant—cryIIIA gene was excised from the resulting plasmid as a HindIII fragment and cloned in the HindIII site of pHT315 (Arantes & Lereclus, 1991, Gene 108, 115–119). For other mutants, pCD digested with the appropriate enzymes was used as vector fragment. This plasmid was constructed by cloning the HindIII fragment of cryIIIA into the HindIII site of pHT315. After purification, the ligation mixture was electroporated in MC1061 E. coli cells. The template for the two primary PCR reactions, the two enzymes used to cut the overlap PCR fragment, the amino acid position and the name of the resulting plasmid are given for all mutants in Table 2. For the construction of a few mutant genes no appropriate 5' restriction enzyme site was available in the cryIIIA gene. We therefore constructed a mutant cryIIIA gene containing a XhoI site at position 1335, resulting in plasmid pCDRE1. The introduction of this site does not change the amino acid sequence of the CryIIIA protein. DNA purified from transformed MC1061 E. coli colonies was used for sequence determination of the region of the gene generated by PCR. Sequencing was performed using the Sanger method (Sanger, 1977, Proc. Natl. Acad. Sci. 74, 5463). Plasmid DNA from a colony containing the correct DNA sequence was then used to transform GM2163 E. coli cells. Plasmid DNA from such E. coli cells was used to electroporate crystal-minus Bt cells (B. thuringiensis subsp. thuringiensis Berliner 1715) (Mahillon et al., 1989, FEMS Microbiol. Lett. 60, 205–210). The resultant transformed Bt cells were grown at 28° C. in T3 medium (trypton 3 g/l, tryptose 2 g/l, yeast extract 1.5 g/l, 5 mg MnCl$_2$, 0.05M Na$_2$DO$_4$, pH 6.8 and 1.5% agar) containing erythromycin (20 μg/ml) until sporulation (usually about 7 days). The medium containing the spore-crystal mixture was harvested and centrifuged. The pellet was washed with a solution containing 0.5M NaCl and 0.1 mM EDTA and subsequently incubated with 50 mM citrate buffer (pH 3) to extract the crystal protein. The extract was filtered over a 0.22 μm filter. The protein concentration was determined using the Bradford method, using BSA as a standard. SDS-PAGE analysis showed that these extracts were essentially pure ICP solutions.

The toxicity of the newly formed mutant proteins towards Diabrotica virgifera virgifera is shown in table 1. Toxicity for Diabrotica was determined as described in Example 3.

CryIIIA proteins having an alanine substitution at each of the amino acids positions 346, 347, 348, 349, 350, 411, 412, 416 and 442 in SEQ ID No. 2, particularly at amino acid positions 349, 350, 411, 412, and 416 in SEQ ID NO. 2, were recognized as "down-mutants" for Diabrotica virgifera virgifera: the toxicity of these mutant proteins for this Diabrotica pest was significantly below the toxicity of the native CryIIIA protein. These positions were found to be located in some of the solvent-exposed loops and beta-strands directed towards or located at the molecular apex of the CryIIIA molecule (Li et al, 1991, supra), more particularly in the part of beta-strand 2 departing from sheet 1 and the loop connecting beta-strand 2 with beta-strand 3r in sheet 1 (Phe346, Gln347, Pro348, Gly349, Tyr350); and in the part of beta-strand 6 departing from sheet 2 and in beta-strand 7r and their connecting loop (Trp411, Pro412, Tyr416), and in the loop connecting beta-strands 8 and 9 (Lys442) in sheet 2. The terminology used above is that from Li et al. (1991, supra).

Alanine-scanning mutagenesis of the Bt109P (also named CryIIID, Lambert et al., 1992, Gene 100, 131–132) protein, based on a model, constructed by computer-assisted amino acid alignment and homology-modelling (see e.g. Swindells, 1992, Current Opinion in Biotechn. 3, 338–347; Bajorath et al., 1993, Protein Science 2, 1798–1810, Felrow and Bryant, 1993, Bio/Technology 11, 479–483) also identifies amino acids involved in corn rootworm toxicity in similar regions of the CryIIID molecule, i.e. at the protruding regions folded towards or located at the predicted apex of the molecule.

Similarly, toxicity analysis of mutants of the CryIH protein (also named Bt2618, PCT publication WO 94/05771) following the above approach also identifies proteins yielding decreased toxicity to Heliothis armigera by substituting individual amino acids located in regions predicted to be protruding from the sheets of domain II, particularly the protruding regions predicted to be located at the apex of the protein.

2. Construction of Random Mutants

The amino acids identified above as yielding down-mutant CryIIIA proteins are now randomly replaced by any of the 20 amino acids (herein named "amino acid randomization"), so as to analyze each identified position for the best performing amino acid (i.e. yielding the most toxic protein).

The procedure to generate random mutants at certain amino acid positions is identical to the procedure used to construct alanine-mutants, except for the primers. In one of the primary PCR reactions, two 'wild type' primers were used. In the other primary PCR reaction, a mutagenic and a wild type primer was used. The mutagenic primer contains an NNG/C codon at the position to be randomized. An 'N' means that the four bases (A,C,G,T) were equally incorporated during oligonucleotide synthesis at this position. 'G/C' means that 50% of the oligonucleotide has a 'G' at this position, whereas the other 50% has a 'C' at this position. The 5' portion of the mutagenic primer used in one of the primary PCR reactions had significant overlap with one of the primers used in the other primary PCR reaction.

By using the above procedures, the amino acid positions identified in Example 1 as being important for Diabrotica toxicity (i.e. yielding a down-mutant protein), and also the neighboring amino acids (in the three-dimensional structure), are randomized. These randomized proteins are tested by the bio-assay of Example 3, and proteins with significantly increased toxicity ("up-mutants") are selected.

Since most amino acids, which upon substitution by alanine are found to result in a down-mutant protein, having a significantly decreased toxicity, are located in the protruding regions located at the apex of the molecule, all amino acids in each of the protruding regions located at the apex of the CryIIIA molecule formed by parts of sheet 1 and 2, as described above, are further replaced by alanine.

Similarly, mutants are designed of the Bt109P and CryIAb proteins, by randomly incorporating amino acids at the amino acid positions identified in Example 2.

3. Toxicity Assays

Because of the difficulties observed with quantitatively assaying *Diabrotica virgifera virgifera* larvae mortality on artificial diet, a new bioassay for Diabrotica, based on feeding inhibition, was developed. Essentially, leaf discs were cut from corn seedlings and were dipped in the toxin dilution. The toxin dilution series of six to eight concentrations were made in an aqueous extract of southern corn rootworm diet (Bioserv F9757, 33 g powder/1 liter water). The toxin solution, obtained as extract from the cells in the citrate buffer of Example 1, was dialyzed against distilled water containing 0.04% (v/v) Triton X-100. This dialysis resulted in the precipitation of the toxin. This suspension is then used to make the dilution series for the bio-assays. No difference in toxicity was recorded between the precipitated toxin suspension and other toxin solutions in citrate buffer on the Colorado potato beetle or on the western corn rootworm. On the western corn rootworm, background mortality was significantly lower with the suspension than with the buffer solution. The dried leaves were placed on Agar in multiwell plates, one leaf with 4 neonate larvae per well. For each concentration, 24 larvae were used. After two days, the size of consumed leaf area was measured. A video camera, with digitizing unit and mounted on a stereomicroscope, was used and the leaf image was analyzed by a personal computer with Aequitas IA Image Analysis Software (Skye Instruments, UK). The aqueous extract of southern corn rootworm diet, with no added toxin, was used as a control. For each toxin the concentration giving 50% feeding inhibition compared to the negative control (EC50) and its 95% confidence interval (CI95) were calculated using Graphpad Prism software (Graphpad, USA). The EC50s of the mutant toxin and of the CryIIIA protein were compared by examining the CI95s. If the intervals overlapped, then the lethal doses did not differ significantly, except under unusual circumstances (Robertson & Preisler, 1991, in Pesticide bioassays with Arthropods, P. 46, CRC Press Inc.). The EC50s and CI95s of the alanine mutants at amino acid positions 349, 350, 411, 412 and 416 of SEQ ID no 2 could not be calculated because of the extreme low toxicity or the lack of toxicity. Because of the extreme large differences in toxicity when compared with the CryIIIA protein, these alanine mutants can be considered as functionally significantly different from the CryIIIA protein.

The results of these bioassays, part of which are shown in Table 1, clearly showed that alanine mutants at amino acid positions 349, 350, 411, 412 and 416 were substantially and significantly less toxic than the CryIIIA protein. The alanine mutants at positions 346, 347, 348, and 442 were found to have a lower toxicity, although not very pronounced, when compared to the native CryIIIA protein. Furthermore, alanine substitutions of amino acids at positions 483, 484, 485, 415, 309, 355, 357, 443, 444, 445, 446, 380, and 322 of SEQ ID no 2 were found not have a significantly different toxicity to the western corn rootworm when compared to the controls (not shown in Table 1).

As a control, mutant proteins were also tested on the Colorado potato beetle, *Leptinotarsa decemlineata* by the potato leaf dip assay described in EP 0458819. The modified CryIIIA protein having the amino acid at position 348 in the CryIIIA protein of SEQ ID no 2 replaced by alanine was found to have a significantly higher toxicity for this insect. Indeed, the $LC_{50}$ value for this ala348 protein was about 5 times lower than that of the native CryIIIA protein. Furthermore, no alanine mutant resulting in a lower corn rootworm toxicity was found to have a significantly lower toxicity for the Colorado potato beetle in all tests. The amino acid positions relevant for toxicity are apparently not the same in the two insects.

Comparative tests on northern corn rootworm larvae using the same methodology as described above show that some of the above identified modified CryIIIA proteins with decreased western corn rootworm toxicity are also significantly less toxic to this insect.

4. Structural Stability of Modified Proteins

We have interpreted a decrease in toxicity of mutant CryIIIA proteins as a proof of the role of the mutated amino acid in toxicity. However, at least from a theoretical point of view, some of the down-mutant proteins may also have a lower toxicity because of aberrant folding of the protein. Gross folding aberrations of down-mutants of this invention are unlikely because of several reasons:

1. All down-mutant proteins have been expressed in a crystal minus *Bt* strain. CryIIIA, like all other ICPs, is produced in *Bt* as a parasporal crystal. All down-mutant proteins were produced as such a crystal.
2. All down-mutants were harvested as crystals from *Bt* and solubilized in citrate buffer. All down-mutants could be solubilized in this buffer.
3. All down-mutants have been analyzed for their reaction with a panel of monoclonal antibodies. These antibodies recognize non-overlapping epitopes on the CryIIIA toxin and are conformationally sensitive as shown by the lack of binding to denatured or reduced toxin in ELISA and the lack of binding to toxin blotted onto nitrocellulose membrane (Western blot). All down-mutant proteins were tested in ELISA and compared with the native CryIIIA protein for their reaction with these monoclonal antibodies. No significant differences in reaction pattern was observed, suggesting that no gross folding aberrations occur in the mutant proteins.
4. The down-mutants, as well as the native CryIIIA protein, have been incubated in vitro with midgut extract from last instar *Diabrotica virgifera virgifera* larvae. The incubation mixtures were then electrophoresed (SDS-PAGE) and blotted onto nitrocellulose membranes. Toxin was detected using polyclonal antibodies, directed against the SDS treated CryIIIA toxin. No differences were observed in the protein band pattern between native CryIIIA and the mutant proteins.
5. All down-mutants were also tested on *Leptinotarsa decemlineata*. No down-mutant showed a significantly lower toxicity on this insect. This indicates that the down-mutants on *D. virgifera virgifera* do not display gross aberrant folding.

Taken together, these data show that the decreased toxicity of the down-mutant proteins of this invention is not likely to be due to gross aberrant folding. It is difficult however to exclude the possibility that some proteins with decreased toxicity display subtle, local alterations in folding which influence toxicity. However this would mean that the mutated residue itself or some neighboring residues are important for toxicity, and thus represent candidates for amino acid randomization in accordance with this invention.

Similarly, the down-mutant CryIIID and CryIH proteins do not show any gross structural distortions.

5. Construction of Modified CryIIIA Protein with Improved Toxicity

Some or all of the best performing amino acids (i.e. yielding the most toxic protein for *Diabrotica virgifera virgifera* of all the randomized mutants at a certain position, as determined by the toxicity assay of Example 3) at the identified positions in the up-mutants are now combined in one modified CryIIIA protein. Analysis of this modified CryIIIA protein in the assay of Example 3 shows that amino acid replacements at the identified positions can significantly increase toxicity of the CryIIIA protein towards *Diabrotica virgifera virgifera*.

Similarly, other modified Cry proteins, such as the CryIIID and CryIAb proteins, show improved toxicity when individual improved amino acids from the different up-mutant proteins are combined in one molecule.

6. Gene Construction and Plant Transformation

A DNA sequence encoding a modified CryIIIA protein of Example 5 is made on an Applied Biosystems 380B DNA synthesizer using standard cyanoethyl phosphoramidite chemistry (or see Davies et al., 1991, supra) and is shown in SEQ ID no 3. The DNA synthesis allows the modification of the coding region to inactivate regions inhibiting expression in corn cells, while still expressing the same protein. The cryIIIA coding region has been optimized in four steps to eliminate elements that might interfere with gene regulation: 1) introduce translation start consensus sequence for plant genes (Joshi, 1987, Nucl. Acids Res. 16, 6643–6653), 2) adapt codons to those preferred in genes of the host cells, i.e. maize genes (Murray et al., 1989, Nucl. Acids res. 2, 477–498), 3) adjust the thus formed sequence to create or eliminate restriction sites to allow proper sequencing and cloning of the gene, 4) eliminate stretches in the DNA sequence, consisting only of G and C nucleotides, of longer than 6 nucleotides, if possible (in the cryIIIA DNA of SEQ ID no 3, two stretches of 8 nucleotides remain, because of the introduction of suitable restriction sites). During steps 2) and 3) CG and TA doublets at codon positions 2 and 3 were avoided, if possible (Murray et al., 1989, supra), to finally generate the cryIIIA sequence of SEQ ID no 3. The amino acid codons marked 'nnn' in SEQ ID no 3, preferably the codons encoding amino acids 350, 351, 412, 413, and 417 in SEQ ID no 4, are replaced by a codon most preferred by corn genes (as chosen from table 4), and encoding an amino acid different from the native amino acid, improving toxicity of the CryIIIA protein to corn rootworm in the assay of Example 3. Also, a truncated modified cryIIIA gene is designed, by replacing the 58 N-terminal codons of the coding region of SEQ ID no 3 by the hexanucleotide 'ATGGCT', thus replacing the 58 N-terminal amino acids of the modified CryIIIA protein by a methionine-alanine dipeptide in the truncated modified CryIIIA protein. This truncated protein has substantially the same insecticidal activity as the full length protein. A chimeric modified cryIIIA gene is constructed by routine plant molecular biology techniques as described in the detailed description. Preferably, the 35S promoter and 35S 3' termination and polyadenylation sequence are used in the chimeric gene for expression in corn. Corn cells are stably transformed by electroporation using wounded and enzyme-degraded embryogenic callus, as described in WO 92/09696 or by using particle-mediated transformation of immature embryos (Koziel et al., 1993, Bio/Technology 11, 194). The resulting transformed cells are selected by means of the incorporated selectable marker gene, grown into plants and tested for susceptibility towards western corn rootworms as described in Example 3. Corn plants expressing the modified CryIIIA protein at the highest levels show a significantly higher protection from corn rootworm damage when compared to the untransformed plants or the plants only transformed with the selectable marker gene. A positive correlation is found between the level of expression, as measured by RNA and protein analysis, and the observed insecticidal effect.

The examples and embodiments of this invention described herein are only supplied for illustrative purposes. Many variations and modifications in accordance with the present invention are known to the person skilled in the art and are included in this invention and the scope of the claims. For instance, it is possible to alter, delete or add some nucleotides or amino acids to the DNA or protein sequences of the invention without departing from the essence of the invention.

All publications (including patent publications) referred to in this application are hereby incorporated by reference.

TABLE 1 toxicity of single alanine replacements at identified positions in CryIIIA towards Diabrotica virgifera virgifera, as identified in the bio-assay of Example 3.

| Mutant | EC50 | CI95% |
|---|---|---|
| Exp1 | | |
| 350 | >243 | |
| 251 | 5.27 | 3.95–7.03 |
| 352 | 4.11 | 0.99–16.93 |
| pSLA | 7.45 | 0.89–62.23 |
| Exp2 | | |
| 353 | 5.21 | 1.89–14.29 |
| 354 | 8.31 | 4.64–14.87 |
| pSLA | 11.60 | 1.84–73.95 |
| Exp3 | | |
| 412 | >243 | |
| 413 | 1.93 | 1.04–3.60 |
| 482 | 1.96 | 0.49–7.75 |
| pSLA | 5.55 | 2.49–12.39 |
| Exp5 | | |
| 411 | >243 | |
| 0 | 4.94 | 1.95–12.56 |
| pSLA | 3.86 | 1.48–10.06 |
| Exp6 | | |
| 406 | 5.50 | 2.22–13.62 |
| 349 | >243 | |
| pSLA | 2.42 | 0.91–6.38 |
| Exp7 | | |
| 311 | 1.09 | 0.42–2.87 |
| 312 | 1.65 | 0.83–.329 |
| pSLA | 1.21 | 0.53–2.74 |
| Exp16 | | |
| 326 | 7.80 | 2.87–21.21 |
| 387 | 4.53 | 1.07–19.04 |
| pSLA | 2.40 | 1.28–4.50 |
| Exp17 | | |
| 384 | 1.32 | 0.37–4.72 |
| 385 | 0.78 | 0.43–1.41 |
| pSLA | 2.88 | 1.36–6.13 |

TABLE 1-continued toxicity of single alanine replacements at identified positions in CryIIIA towards Diabrotica virgifera virgifera, as identified in the bio-assay of Example 3.

| Mutant | EC50 | CI95% |
|---|---|---|
| Exp18 | | |
| 448 | 11.52 | 7.05–18.85 |
| 449 | 7.12 | 4.40–11.52 |
| pSLA | 4.04 | 1.56–10.52 |
| Exp20 | | |
| 310 | 0.30 | 0.07–1.31 |
| 313 | 0.33 | 0.08–1.34 |
| pSLA | 1.39 | 0.58–6.49 |
| Exp22 | | |
| 408 | 4.29 | 2.14–8.60 |
| 348 | 12.47 | 3.38–45.92 |
| pSLA | 3.08 | 2.31–4.12 |
| Exp23 | | |
| 376 | 0.39 | 0.02–7.23 |
| 377 | 0.51 | 0.11–2.43 |
| pSLA | 0.71 | 0.41–1.23 |
| Exp24 | | |
| 375 | 1.65 | 1.06–2.57 |
| pSLA | 0.95 | 0.95–1.31 |
| Exp25 | | |
| 416 | >256 | |
| 327 | 2.40 | 0.94–6.14 |
| pSLA | 3.82 | 1.13–12,81 |

"Mutant" refers to the amino acid position in the CryIIIA protein of SEQ ID no 2 (hold ones are clear down-mutants), or to the native CryIIIA protein ("pSLA")

"EC50" represents the concentration at which 50% feeding inhibition was observed, expressed in microgram/ml "CI95%" represents the 95% confidential intervals of the EC50 values

TABLE 2

PCR templates and restriction enzymes used in Example 1.

| AAPOS | TEMPLATE | ENZYME 1 | ENZYME 2 | PLASMID | AAPOS | TEMPLATE | ENZYME 1 | ENZYME 2 | PLASMID |
|---|---|---|---|---|---|---|---|---|---|
| 350 | pBT3A2 | Bsu36I | PflMI | pY350A | 418 | PBT3A2 | PflMI | BclI | pG418A |
| 351 | pBT3A2 | Bsu36I | PflMI | pY351A | 419 | pBT3A2 | PflMI | BclI | pV419A |
| 352 | pBT3A2 | Bsu36I | PflMI | pG352A | 349 | pBT3A2 | Bsu36I | PflMI | pG349A |
| 353 | pBT3A2 | Bsu36I | PflMI | pN353A | 348 | pBT3A2 | Bsu36I | PflMI | pP348A |
| 354 | pBT3A2 | Bsu36I | PflMI | pD354A | 347 | pBT3A2 | Bsu36I | PflMI | pQ347A |
| 412 | pBt3A2 | PflMI | BclI | pP412A | 346 | pBT3A2 | Bsu36I | PflMI | pF346A |
| 413 | pBT3A2 | PflMI | BclI | pS413A | 355 | pBT3A2 | Bsu36I | PflMI | pS355A |
| 481 | pBT3A2 | BclI | XcmI | pM481A | 356 | pBT3A2 | Bsu36I | PflMI | pF356A |
| 482 | pBT3A2 | BclI | XcmI | pQ482A | 357 | pBT3A2 | Bsu36I | PflMI | pN357A |
| 483 | pBT3A2 | BclI | XcmI | pG483A | 358 | pBT3A2 | Bsu36I | PflMI | pY358A |
| 484 | pBT3A2 | BclI | XcmI | pS484A | 441 | pBT3A2 | BclI | XcmI | pS441A |
| 485 | pBT3A2 | BclI | XcmI | pR485A | 442 | pBT3A2 | CclI | XcmI | pK442A |
| 486 | pBT3A2 | BclI | XcmI | pG486A | 443 | pBT3A2 | BclI | XcmI | pR443A |
| 410 | pBt3A2 | PflMI | BclI | pV410A | 444 | pBT3A2 | BclI | XcmI | pN444A |
| 411 | pBT3A2 | PflMI | BclI | pW411A | 445 | pBT3A2 | BclI | XcmI | pV445A |
| 415 | pBT3A2 | PflMI | BclI | pV415A | 446 | pBT3A2 | BclI | XcmI | pG446A |
| 309 | pCDRE1 | XhoI | Bsu36I | pV309A | 448 | pBT3A2 | BclI | XcmI | pV448A |
| 310 | pCDRE1 | XhoI | Bsu36I | pG310A | 449 | pBT3A2 | BclI | XcmI | pS449A |
| 311 | pCDRE1 | XhoI | Bsu36I | pV311A | 383 | pBT3A2 | Bsu36I | BclI | pN383A |
| 312 | pCDRE1 | XhoI | Bsu36I | pN312A | 384 | pBT3A2 | Bsu36I | BclI | pK384A |
| 313 | pCDRE1 | XhoI | PflMI | pN313A | 385 | pBT3A2 | Bsu36I | BclI | pS365A |
| 406 | pBT3A2 | PflMI | BclI | pT406A | 386 | pBT3A2 | Bsu36I | BclI | pS386A |
| 407 | pBT3A2 | PflMI | BclI | pN407A | 387 | pBT3A2 | Bsu36I | BclI | pE387A |
| 408 | pBT3A2 | PflMI | BclI | pL408A | 373 | pBT3A2 | Bsu36I | PflNI | pN373A |
| 416 | pBT3A2 | PflMI | BclI | pY416A | 374 | pBT3A2 | Bsu36I | PflMI | pD374A |
| 417 | pBT3A2 | PflMI | BclI | pS417A | 375 | pBT3A2 | Bsu36I | PflMI | pI375A |
| 376 | pBT3A2 | Bsu36I | PflMI | pI376A | | | | | |
| 377 | pBT3A2 | Bsu36I | PflMI | pT377A | | | | | |
| 380 | pBT3A2 | Bsu36I | BclI | pF380A | | | | | |
| 315 | pCDRE1 | XhoI | PflMI | pR315A | | | | | |
| 316 | pBT3A2 | Bsu36I | PflMI | pG316A | | | | | |
| 320 | pBT3A2 | Bsu36I | PflMI | pT320A | | | | | |
| 321 | pBT3A2 | Bsu36I | PflMI | pF321A | | | | | |
| 322 | pBT3A2 | Bsu36I | PflMI | pS322A | | | | | |
| 326 | pBT3A2 | Bsu36I | PflMI | pN326A | | | | | |
| 327 | pBT3A2 | Bsu36I | PflMI | pY327A | | | | | |
| 330 | pBT3A2 | Bsu36I | PflMI | pK330A | | | | | |
| 332 | pBT3A2 | Bsu36I | PflMI | pH332A | | | | | |

TABLE 3 relative solvent accessibility of amino acid side chains of positions 291 to 506.
(POS: amino acid position in the CryIIIA protein of SEQ ID no 2, ACC: relative solvent accessibility)

| POS | ACC | POS | ACC | POS | ACC | POS | ACC | POS | ACC | POS | ACC | POS | ACC | POS | ACC |
|---|---|---|---|---|---|---|---|---|---|---|---|---|---|---|---|
| 291 | 2 | 318 | 1 | 345 | 25 | 372 | 12 | 399 | 0 | 426 | 0 | 453 | 13 | 480 | 26 |
| 292 | 35 | 319 | 0 | 346 | 44 | 373 | 73 | 400 | 8 | 427 | 9 | 454 | 31 | 481 | 1 |
| 293 | 37 | 320 | 24 | 347 | 1 | 374 | 61 | 401 | 12 | 428 | 16 | 455 | 2 | 482 | 37 |
| 294 | 11 | 321 | 6 | 348 | 31 | 375 | 45 | 402 | 0 | 429 | 35 | 456 | 0 | 483 | 71 |
| 295 | 1 | 322 | 41 | 349 | 8 | 376 | 35 | 403 | 19 | 430 | 64 | 457 | 0 | 484 | 59 |
| 296 | 24 | 323 | 31 | 350 | 40 | 377 | 47 | 404 | 0 | 431 | 54 | 458 | 3 | 485 | 17 |
| 297 | 3 | 324 | 3 | 351 | 61 | 378 | 4 | 405 | 8 | 432 | 62 | 459 | 14 | 486 | 1 |
| 298 | 0 | 325 | 18 | 352 | 48 | 379 | 56 | 406 | 7 | 433 | 63 | 460 | 25 | 487 | 0 |
| 299 | 2 | 326 | 56 | 353 | 75 | 380 | 47 | 407 | 3 | 434 | 34 | 461 | 65 | 488 | 1 |
| 300 | 2 | 327 | 48 | 354 | 25 | 381 | 12 | 408 | 47 | 435 | 33 | 462 | 80 | 489 | 1 |
| 301 | 9 | 328 | 15 | 355 | 7 | 382 | 6 | 409 | 1 | 436 | 49 | 463 | 27 | 490 | 0 |
| 302 | 25 | 329 | 16 | 356 | 0 | 383 | 24 | 410 | 59 | 437 | 26 | 464 | 47 | 491 | 1 |
| 303 | 0 | 330 | 47 | 357 | 0 | 384 | 59 | 411 | 18 | 438 | 26 | 465 | 39 | 492 | 0 |
| 304 | 1 | 331 | 19 | 358 | 6 | 385 | 73 | 412 | 57 | 439 | 12 | 466 | 13 | 493 | 0 |
| 305 | 0 | 332 | 35 | 359 | 0 | 386 | 33 | 413 | 85 | 440 | 19 | 467 | 62 | 494 | 1 |
| 306 | 3 | 333 | 10 | 360 | 0 | 387 | 28 | 414 | 10 | 441 | 0 | 468 | 1 | 495 | 2 |
| 307 | 1 | 334 | 4 | 361 | 0 | 388 | 47 | 415 | 13 | 442 | 57 | 469 | 0 | 496 | 28 |
| 308 | 0 | 335 | 1 | 362 | 0 | 389 | 48 | 416 | 18 | 443 | 42 | 470 | 2 | 497 | 17 |
| 309 | 13 | 336 | 3 | 363 | 24 | 390 | 22 | 417 | 2 | 444 | 46 | 471 | 0 | 498 | 2 |
| 310 | 15 | 337 | 2 | 364 | 0 | 391 | 28 | 418 | 2 | 445 | 37 | 472 | 0 | 499 | 10 |
| 311 | 7 | 338 | 16 | 365 | 0 | 392 | 12 | 419 | 0 | 446 | 24 | 43 | 1 | 500 | 19 |
| 312 | 83 | 339 | 22 | 366 | 0 | 393 | 35 | 420 | 0 | 447 | 65 | 474 | 0 | 501 | 36 |
| 313 | 43 | 340 | 0 | 367 | 24 | 394 | 1 | 421 | 19 | 448 | 42 | 475 | 3 | 502 | 0 |
| 314 | 0 | 341 | 9 | 368 | 3 | 395 | 53 | 422 | 0 | 449 | 50 | 476 | 2 | 503 | 21 |
| 315 | 58 | 342 | 1 | 369 | 0 | 396 | 41 | 423 | 14 | 450 | 13 | 477 | 2 | 504 | 0 |
| 316 | 56 | 343 | 6 | 370 | 22 | 397 | 17 | 424 | 1 | 451 | 28 | 478 | 0 | 505 | 12 |
| 317 | 30 | 344 | 0 | 371 | 18 | 398 | 7 | 425 | 0 | 452 | 0 | 479 | 6 | 506 | 12 |

TABLE 4

Most preferred codons for amino acid codon replacement in artificial modified Bt ICP coding regions, e.g. the modified CryIIIA coding region of SEQ ID no 3, for expression in plants, such as corn (from Murray et al., 1989, supra).

| | |
|---|---|
| Arg | CGC |
| Leu | CTG |
| Ser | AGC |
| Thr | ACC |
| Pro | CCC |
| Ala | GCC |
| Gly | GGC |
| Val | GTG |
| Lys | AAG |
| Asn | AAC |
| Gln | CAG |
| His | CAC |
| Glu | GAG |
| Asp | GAC |
| Tyr | TAC |
| Cys | TGC |
| Phe | TTC |
| Ile | ATC |
| Met | ATG |
| Trp | TGG |

We claim:

1. A recombinant or synthetic DNA sequence encoding a modified CryIII protein, which modification comprises replacing an amino acid occurring at at least one position of said CryIII protein with a different amino acid, said replaced amino acid being (1) an amino acid located in domain II and having a relative solvent accessibility of at least 40% or (2) located at a maximum distance, in the primary sequence, of 3 positions from an amino acid having at least 40% relative solvent-accessibility in domain II, wherein said modified CryIII protein has an increased toxicity to a Coleopteran insect.

2. The DNA of claim 1 wherein the Coleopteran insect is a Colorado potato beetle or a corn rootworm.

3. The DNA of claim 1 wherein said at least one position is located in a protruding region oriented towards the apex of the molecule or located at the apex of the molecule.

4. The DNA of claim 3, wherein said at least one position is located at the apex of the molecule.

5. The DNA of claim 1 in which said CryIII protein contains domain II of the CryIIIA protein.

6. The DNA of claim 1 in which said modified CryIII protein has an altered toxicity to *Diabrotica virgifera virgifera*.

7. The DNA of claim 6 in which said CryIII protein is a CryIIIA protein.

8. The DNA of claim 6 in which said replaced amino acid is selected from the group consisting of: Phe346, Gln347, Pro348, Gly349, Try350, Trp411, Pro412, Try416, Lys442 in SEQ ID no 2, or any amino acid immediately adjacent, the C-alpha atom of which is located at a maximum distance of 7 angstroms from the C-alpha atom of one of these two amino acids in the three-dimensional structure of the protein.

9. The DNA of claim 6 in which said replaced amino acid is selected from the group consisting of: Phe346, Gln347, Pro348, Gly349, Tyr350, Trp411, Pro412, Tyr416, Lys442 in SEQ ID no 2.

10. The DNA of claim 6 in which said replaced amino acid is selected from the group consisting of: Gly349, Tyr350, Trp411, Pro412, Tyr416 in SEQ ID no 2.

11. The DNA of claim 9 which has the sequence shown in SEQ ID no 3, wherein 'nnn' is a codon selected from Table 4.

12. The DNA of claim 11, wherein at least one of the 'nnn' codons encodes alanine.

13. A plant or a seed including incorporated in its genome, a chimeric gene comprising the recombinant or synthetic DNA of claim 1 operably linked to regulatory sequences allowing expression in cells of said plant.

14. The plant or seed of claim 13 which is a corn plant or seed.

15. The modified CryIII protein encoded by the DNA of claim 1.

16. A method for improving the toxicity of a CryIIIA protein for corn rootworm pests, said method comprising changing at least one of the amino acids marked with Xaa in SEQ ID No. 4 by another amino acid, so that the modified CryIIIA protein has an increased toxicity towards corn rootworms.

17. A method for improving the toxicity of a Cry III protein towards a pest insect, the method comprising the following steps:

1a) scanning a Cry III protein for amino acid positions with at least 40% relative solvent-accessibility in domain II and neighboring amino acids in domain II, at a maximum distance of 3 positions, in the primary sequence, from said amino acids in the primary sequence, or 1b) scanning a Cry III protein for amino acids at positions structurally analogous to amino acid positions in domain II of CryIIIA with at least 40% relative solvent accessibility and at neighboring amino acid positions in domain II of said CryIII protein, wherein said neighboring amino acid positions are at a maximum distance of 3 positions, in the primary sequence, from said structurally analogous amino acid positions, 2) replacing these identified amino acid positions by alanine in different proteins; one amino acid is replaced by one alanine in each protein, 3) selecting proteins obtained in 2) with a significant drop in toxicity to the target insect without causing gross structural distortion in the protein, 4) replacing randomly the alanine amino acid in the selected proteins of 3) by any other amino acid, 5) selecting those proteins obtained in 4) having improved toxicity to the target insect, and 6) combining all or most of the amino acids, yielding the highest toxicity for said target insect at a certain position in the *Bt* protein, in one protein with superior toxicity to said insect.

18. A DNA sequence encoding at least a modified CryIIIA toxin with improved toxicity to the Colorado potato beetle, wherein said modified CryIIIA toxin has the proline amino acid at position 348 in SEQ ID no 2 replaced by alanine.

19. A process for combatting the Colorado potato beetle, which comprises contacting this insect with a modified CryIIIA protein encoded by the DNA sequence of claim 18.

20. A method of improving plant resistance towards an insect pest comprising applying the protein obtained by the process of claim 17 to said plant.

21. A recombinant synthetic DNA sequence encoding a modified CryIII protein, which modification comprises replacing an amino acid occurring at least one position of said CryIII protein with a different amino acid, said replaced amino acid being (1) an amino acid located in domain II at a position structurally analogous to amino acids with a relative solvent accessibility of at least 40% in CryIIIA or (2) located at a maximum distance, in the primary sequence, of 3 positions from an amino acid having such a structurally analogous position in domain II, wherein said modified CryIII protein has an increased toxicity to a Coleopteran insect.

* * * * *